(12) United States Patent
Shelton, IV et al.

(10) Patent No.: US 12,154,683 B2
(45) Date of Patent: Nov. 26, 2024

(54) INTERCOMMUNICATION AND COOPERATIVE OPERATION OF SURGICAL DEVICES

(71) Applicant: Cilag GmbH International, Zug (CH)

(72) Inventors: Frederick E. Shelton, IV, Hillsboro, OH (US); Shane R. Adams, Lebanon, OH (US); Kevin Fiebig, Cincinnati, OH (US); Jeffrey D. Messerly, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 207 days.

(21) Appl. No.: 17/384,455

(22) Filed: Jul. 23, 2021

(65) Prior Publication Data

US 2023/0026893 A1 Jan. 26, 2023

Related U.S. Application Data

(60) Provisional application No. 63/224,813, filed on Jul. 22, 2021.

(51) Int. Cl.
*G16H 40/40* (2018.01)
*A61B 17/00* (2006.01)
(Continued)

(52) U.S. Cl.
CPC ............ *G16H 40/20* (2018.01); *A61B 17/00* (2013.01); *A61B 18/1206* (2013.01); *A61B 34/10* (2016.02); *A61B 34/20* (2016.02); *A61B 34/25* (2016.02); *A61B 34/30* (2016.02); *A61B 34/32* (2016.02); *A61B 90/08* (2016.02); *A61B 90/37* (2016.02); *G05B 13/0265* (2013.01); *G06F 3/14* (2013.01); *G06F 3/1423* (2013.01);
(Continued)

(58) Field of Classification Search
None
See application file for complete search history.

(56) References Cited

U.S. PATENT DOCUMENTS 5,652,866 A * 7/1997 Aldred ................ H04L 12/1813
703/23
6,766,373 B1 7/2004 Beadle et al.
(Continued)

FOREIGN PATENT DOCUMENTS

EP 1010230 B1 10/2003
EP 3506287 A1 7/2019
WO 2019119130 A1 6/2019

OTHER PUBLICATIONS

Jagannath, et al., "An Analysis of Speech as a Modality for Activity Recognition during Complex Medical Teamwork", Pervasive Computing Technologies for Healthcare, May 2018, pp. 1-10.

*Primary Examiner* — John A Pauls
(74) *Attorney, Agent, or Firm* — Condo Roccia Koptiw LLP

(57) ABSTRACT

Examples described herein any include a surgical module for use within the surgical system. The surgical module may include a first port connected to a surgical hub; a second port connected to an additional surgical module; and a controller. The controller may be configured to receive surgical data; determine if the surgical data is a first type of data or a second type of data; and instruct the surgical module to send the surgical data to the first port if the surgical data is the first type of data or to the second port if the surgical data is the second type of data.

20 Claims, 26 Drawing Sheets

(51) Int. Cl.

| | | |
|---|---|---|
| A61B 18/12 | (2006.01) | |
| A61B 34/00 | (2016.01) | |
| A61B 34/10 | (2016.01) | |
| A61B 34/20 | (2016.01) | |
| A61B 34/30 | (2016.01) | |
| A61B 34/32 | (2016.01) | |
| A61B 90/00 | (2016.01) | |
| G05B 13/02 | (2006.01) | |
| G06F 3/14 | (2006.01) | |
| G06F 3/16 | (2006.01) | |
| G06F 9/48 | (2006.01) | |
| G06F 9/54 | (2006.01) | |
| G06F 13/40 | (2006.01) | |
| G06F 16/21 | (2019.01) | |
| G06F 16/28 | (2019.01) | |
| G06N 20/00 | (2019.01) | |
| G06Q 10/30 | (2023.01) | |
| G06T 11/60 | (2006.01) | |
| G08B 5/22 | (2006.01) | |
| G10L 15/22 | (2006.01) | |
| G16H 10/60 | (2018.01) | |
| G16H 15/00 | (2018.01) | |
| G16H 20/40 | (2018.01) | |
| G16H 30/40 | (2018.01) | |
| G16H 40/20 | (2018.01) | |
| G16H 40/63 | (2018.01) | |
| G16H 40/67 | (2018.01) | |
| G16H 50/20 | (2018.01) | |
| G16H 50/70 | (2018.01) | |
| H04L 1/22 | (2006.01) | |
| H04L 41/12 | (2022.01) | |
| H04L 65/80 | (2022.01) | |
| H04L 67/12 | (2022.01) | |
| H04L 67/125 | (2022.01) | |
| H04N 5/272 | (2006.01) | |
| H04N 7/15 | (2006.01) | |
| A61B 8/06 | (2006.01) | |
| A61B 18/00 | (2006.01) | |
| G06F 21/62 | (2013.01) | |
| G06F 40/169 | (2020.01) | |
| G16H 30/20 | (2018.01) | |
| H02J 7/00 | (2006.01) | |

(52) U.S. Cl.
CPC ............ *G06F 3/167* (2013.01); *G06F 9/4881* (2013.01); *G06F 9/542* (2013.01); *G06F 13/4068* (2013.01); *G06F 16/211* (2019.01); *G06F 16/284* (2019.01); *G06F 16/285* (2019.01); *G06N 20/00* (2019.01); *G06Q 10/30* (2013.01); *G06T 11/60* (2013.01); *G08B 5/22* (2013.01); *G10L 15/22* (2013.01); *G16H 10/60* (2018.01); *G16H 15/00* (2018.01); *G16H 20/40* (2018.01); *G16H 30/40* (2018.01); *G16H 40/40* (2018.01); *G16H 40/63* (2018.01); *G16H 40/67* (2018.01); *G16H 50/20* (2018.01); *G16H 50/70* (2018.01); *H04L 1/22* (2013.01); *H04L 41/12* (2013.01); *H04L 65/80* (2013.01); *H04L 67/12* (2013.01); *H04L 67/125* (2013.01); *H04N 5/272* (2013.01); *H04N 7/15* (2013.01); *A61B 8/06* (2013.01); *A61B 2017/00221* (2013.01); *A61B 2018/00702* (2013.01); *A61B 2018/00994* (2013.01); *A61B 2034/2072* (2016.02); *A61B 2034/254* (2016.02); *A61B 2090/364* (2016.02); *A61B 2090/365* (2016.02); *A61B 2090/373* (2016.02); *G06F 21/6245* (2013.01); *G06F 40/169* (2020.01); *G10L 2015/223* (2013.01); *G16H 30/20* (2018.01); *H02J 7/0063* (2013.01)

(56) References Cited

U.S. PATENT DOCUMENTS

| | | |
|---|---|---|
| 8,565,073 B2 | 10/2013 | Rahman et al. |
| 8,908,678 B1 | 12/2014 | Mcgonigal et al. |
| 9,011,427 B2 | 4/2015 | Price et al. |
| 9,283,054 B2 | 3/2016 | Morgan et al. |
| 9,345,481 B2 | 5/2016 | Hall et al. |
| 11,146,690 B2 | 10/2021 | Minert |
| 2002/0000464 A1 | 1/2002 | Ramberg et al. |
| 2005/0210070 A1 | 9/2005 | Macneil |
| 2007/0140235 A1* | 6/2007 | Aysan ............... H04L 45/60 370/389 |
| 2014/0160259 A1 | 6/2014 | Blanquart et al. |
| 2014/0160260 A1 | 6/2014 | Blanquart et al. |
| 2014/0263552 A1 | 9/2014 | Hall et al. |
| 2014/0267655 A1 | 9/2014 | Richardson et al. |
| 2015/0119035 A1 | 4/2015 | Ganu et al. |
| 2015/0128274 A1 | 5/2015 | Giokas |
| 2017/0296213 A1 | 10/2017 | Swensgard et al. |
| 2018/0344308 A1 | 12/2018 | Nawana et al. |
| 2018/0360452 A1 | 12/2018 | Shelton, IV et al. |
| 2019/0104919 A1* | 4/2019 | Shelton, IV ......... A61B 34/37 |
| 2019/0191963 A1 | 6/2019 | Kuhn et al. |
| 2019/0200844 A1 | 7/2019 | Shelton, IV et al. |
| 2019/0200906 A1 | 7/2019 | Shelton, IV et al. |
| 2019/0200980 A1 | 7/2019 | Shelton, IV et al. |
| 2019/0200988 A1 | 7/2019 | Shelton, IV |
| 2019/0201033 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201115 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201129 A1 | 7/2019 | Shelton, Iv et al. |
| 2019/0201137 A1 | 7/2019 | Shelton, IV et al. |
| 2019/0201140 A1 | 7/2019 | Yates et al. |
| 2019/0204201 A1 | 7/2019 | Shelton, IV et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206556 A1 | 7/2019 | Shelton, IV et al. |
| 2019/0206562 A1 | 7/2019 | Shelton, IV et al. |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0333626 A1 | 10/2019 | Mansi et al. |
| 2020/0008044 A1 | 1/2020 | Poornachandran et al. |
| 2021/0205031 A1 | 7/2021 | Shelton, IV |
| 2021/0212717 A1 | 7/2021 | Yates et al. |
| 2022/0020476 A1 | 1/2022 | Souissi |
| 2022/0046292 A1 | 2/2022 | Nair et al. |
| 2022/0104713 A1 | 4/2022 | Shelton, IV |
| 2022/0104896 A1 | 4/2022 | Shelton, IV et al. |
| 2022/0104910 A1 | 4/2022 | Shelton, IV et al. |
| 2022/0108789 A1 | 4/2022 | Shelton, IV et al. |
| 2022/0233119 A1 | 7/2022 | Shelton, IV et al. |
| 2022/0233135 A1 | 7/2022 | Shelton, IV et al. |
| 2022/0233136 A1 | 7/2022 | Shelton, IV et al. |
| 2022/0233151 A1 | 7/2022 | Shelton, IV et al. |
| 2022/0233191 A1 | 7/2022 | Shelton, IV et al. |
| 2022/0233252 A1 | 7/2022 | Shelton, IV et al. |
| 2022/0233254 A1 | 7/2022 | Shelton, IV et al. |
| 2022/0238216 A1 | 7/2022 | Shelton, IV et al. |

(56) References Cited

U.S. PATENT DOCUMENTS

| | | |
|---|---|---|
| 2022/0240869 A1 | 8/2022 | Shelton, IV et al. |
| 2022/0241028 A1 | 8/2022 | Shelton, IV et al. |
| 2022/0241474 A1 | 8/2022 | Shelton, IV et al. |
| 2022/0303945 A1 | 9/2022 | Tsuda |
| 2023/0021920 A1 | 1/2023 | Shelton, IV et al. |
| 2023/0023635 A1 | 1/2023 | Shelton, IV et al. |
| 2023/0035775 A1 | 2/2023 | Kohada |

* cited by examiner

INTERCOMMUNICATION AND COOPERATIVE OPERATION OF SURGICAL DEVICES

CROSS-REFERENCE TO RELATED APPLICATIONS

This application claims the benefit of Provisional U.S. Patent Application No. 63/224,813, filed Jul. 22, 2021, the disclosure of which is incorporated herein by reference in its entirety.

This application is related to the following, filed contemporaneously, the contents of each of which are incorporated by reference herein:

U.S. patent application Ser. No. 17/384,274, filed Jul. 23, 2021, titled METHOD OF SURGICAL SYSTEM POWER MANAGEMENT, COMMUNICATION, PROCESSING, STORAGE AND DISPLAY U.S. patent application Ser. No. 17/384,453, filed Jul. 23, 2021, titled MONITORING POWER UTILIZATION AND NEEDS WITHIN SURGICAL SYSTEMS U.S. patent application Ser. No. 17/384,457, filed Jul. 23, 2021, titled DETECTION OF SURGICAL DEVICES WITHIN SURGICAL SYSTEMS

BACKGROUND

Surgical procedures are typically performed in surgical operating theaters or rooms in a healthcare facility such as, for example, a hospital. Various surgical devices and systems are utilized in performance of a surgical procedure. In the digital and information age, medical systems and facilities are often slower to implement systems or procedures utilizing newer and improved technologies due to patient safety and a general desire for maintaining traditional practices. It is desirable to improve the delivery and processing of surgical devices within the surgical system.

SUMMARY

Examples described herein may include a surgical power device configured to balance power needs. The surgical power device may include a first output power interface configured to supply a first surgical module having a first power expectation; a second output power interface configured to supply a second surgical module having a second power expectation; a power distribution unit configured to receive operating room power, to provide a first portion of the operating room power to the first output power interface, and to provide a second portion of the operating room power to the second output power interface; and a controller in communication with the power distribution unit. The controller may be configured to determine an available amount of operating room power, the first power expectation, and the second power expectation; determine a power budget for the first surgical module and the second surgical module based on the available amount of operating room power, the first power expectation, and the second power expectation; and control the power distribution unit, based on the power budget, to set the first portion of the operating room power and the second portion of the operating room power.

Examples described herein may include methods of balancing operating room power supplied to a power distribution unit within a surgical system. The method may determine a first power expectation associated with a first surgical module, a second power expectation associated with a second surgical module, and an available amount of operating room power within an operating room; a power budget for the first surgical module and the second surgical module based on the available amount of operating room power, the first power expectation, and the second power expectation; and control the power distribution unit, based on the power budget, to a set a first portion and a second portion of the operating room power supplied to the power distribution unit. The first portion of the operating room power may be provided to a first output power interface configured to supply the first surgical module and second portion of the operating room power may be provided to a second output power interface configured to supply the second surgical module.

Examples described herein may include a surgical system configured to balance power needs. The surgical system may include a power facility, a surgical network, a surgical power unit, and a communications interface. The surgical power unit may include a first output-power interface configured to supply a first surgical module having a first power expectation; a second output-power interface configured to supply a second surgical module having a second power expectation; a power distribution unit configured to receive operating-room power from the power facility, to provide a first portion of the operating-room power to the first output-power interface, and to provide a second portion of the operating-room power to the second output-power interface; and a controller in communication with the power distribution unit. The controller may determine an available amount of operating-room power, the first power expectation, and the second power expectation; determine a power budget for the first surgical module and the second surgical module based on the available amount of operating-room power, the first power expectation, and the second power expectation; and control the power distribution unit, based on the power budget, to set the first portion of the operating-room power and the second portion of the operating-room power. The communications interface may be in communication with the power facility and the surgical network. The communications interface may communicate the first portion and the second portion of the operating-room power to the power facility and the surgical network.

Examples described herein any include a surgical module for use within the surgical system. The surgical module may include a first port connected to a surgical hub; a second port connected to an additional surgical module; and a controller. The controller may be configured to receive surgical data; determine if the surgical data is a first type of data or a second type of data; and instruct the surgical module to send the surgical data to the first port if the surgical data is the first type of data or to the second port if the surgical data is the second type of data.

In examples, the surgical module may include a first port connected to a surgical hub; a second port connected to an additional surgical module; and a controller. The controller may be configured to receive surgical data; determine if the surgical data is a first type of data or a second type of data; instruct the surgical module to send the surgical data to the first port if the surgical data is the first type of data or to the second port if the surgical data is the second type of data; exclude control of the first type of data; and simultaneously control the second type of data.

Examples described herein may include a surgical system that provides intercommunication and cooperative operating of surgical devices. The surgical system may include a surgical hub, a surgical power system configured to power the surgical hub, and a surgical module. The surgical module may include a first port connected to the surgical hub; a second port connected to an additional surgical module; and a controller. The controller may be configured to receive surgical data from the surgical hub; determine if the surgical data is a first type of data or a second type of data; and instruct the surgical module to send the surgical data to the first port if the surgical data is the first type of data or to the second port if the surgical data is the second type of data.

Examples described herein may include a surgical computing device that directs data communications to surgical networks. The surgical computing device may include a processor that is configured to determine a present network locus, wherein the present network locus is any of a first surgical network or a second surgical network; identify a data communications session; determine a surgical data type of the data communication session, wherein the surgical data type is any of a first type of surgical data or a second type of surgical data, and direct the data communications session to the first surgical network if the surgical data type is the first type of surgical data or to the second surgical network if the surgical data type is the second type of surgical data. In examples, the surgical computing device may include a processor that is configured to determine a present network locus of the processor; wherein the present network locus is any of a first surgical network or a second surgical network; identify a data communications session, determine a surgical data type of the data communication session; and direct the data communications session to the first surgical network or the second surgical network based on the present network locus and the surgical data type of the data communication session.

Examples described herein may include a surgical system that directs data communications to surgical networks. The surgical system may include a surgical hub, a plurality of surgical modules, a first plurality of functions within a first surgical network, wherein the first surgical network is associated with a first type of surgical data; a second plurality of functions within a second surgical network, wherein the second surgical network is associated with a second type of surgical data; a processor of the surgical hub; and a processor of at least one of the surgical modules. The processor of the surgical hub may be configured to combine at least one of the first plurality of functions with at least one of the second plurality of functions to create a third surgical network, wherein the third surgical network is connected to the surgical hub and associated with a third type of surgical data. The processor of the at least one surgical module may be configured to determine a present network locus of the processor, wherein the present network locus is any of the first surgical network, the second surgical network, or the third surgical network; identify a data communications session; determine a surgical data type of the data communication session, wherein the surgical data type is any of a first type of surgical data, a second type of surgical data, or a third type of surgical data, and direct the data communications session to the third surgical network if the surgical data type is the third type of surgical data.

DETAILED DESCRIPTION

Figure 1A:
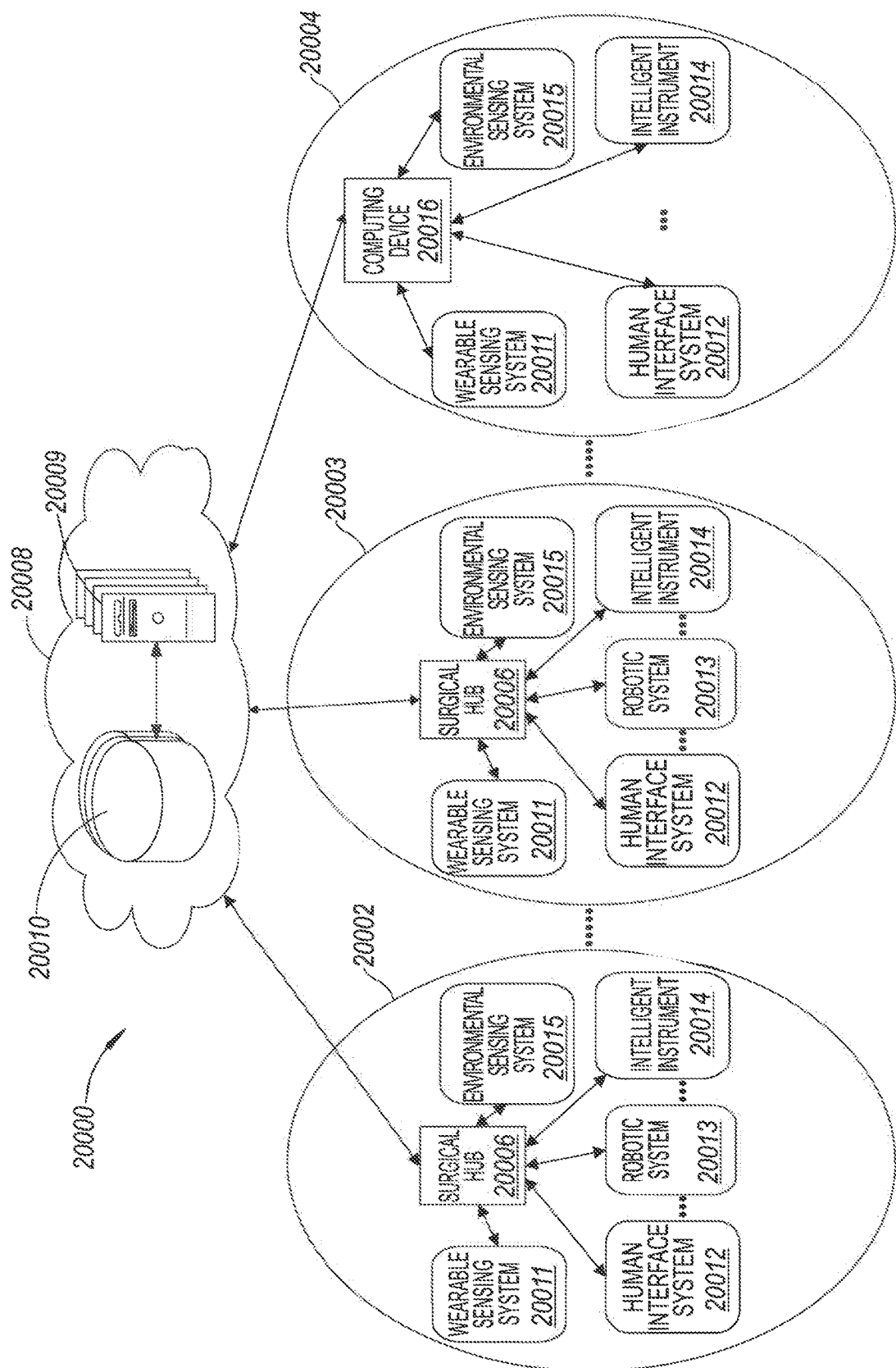
FIG. 1A is a block diagram of a computer-implemented surgical system.

FIG. 1A is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1A. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 1B:
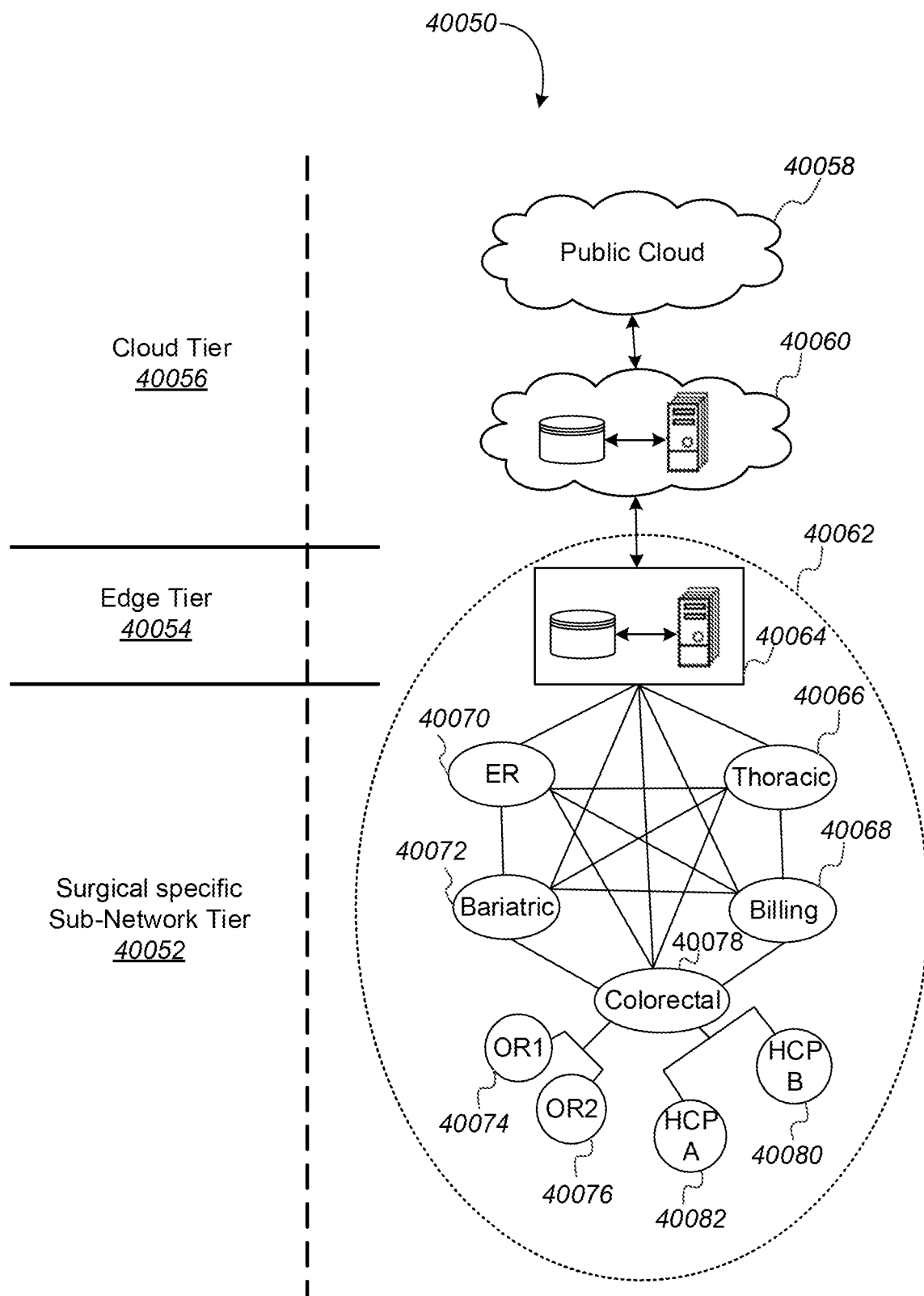
FIG. 1B is a block diagram of a computer-implemented multi-tier surgical system.

FIG. 1B is a block diagram of a computer-implemented multi-tier surgical system. As illustrated in FIG. 1B, a computer-implemented multi-tier surgical system 40050 may include multiple tiers of systems, such as a surgical specific sub-network tier system 40052, an edge tier system 40054 that is associated with the surgical specific sub-network tier system 40052, and a cloud tier system 40056.

A surgical specific sub-network tier system 40052 may include a plurality of inter-connected surgical sub-systems. For example, the surgical sub-systems may be grouped by the type of surgical procedures and/or other departments in a medical facility or a hospital. For example, a medical facility or a hospital may include a plurality of surgical procedure specific departments, such as an emergency room (ER) department 40070, colorectal department 40078, bariatric department 40072, thoracic department 40066, and billing department 40068. Each of the surgical procedure specific departments may include one or more surgical sub-systems associated with an operating room (OR) and/or a healthcare care professional (HCP). For example, the colorectal department 40078 may include a set of surgical hubs (e.g., surgical hub 20006 as described in FIG. 1A). The surgical hubs may be designated for a respective HCP, such as HCP A, 40082 and HCP B, 40080. In an example, the colorectal department may include a group of surgical hubs that may be located in respective ORs, such as OR 1, 40074 and OR 2, 40076. The medical facility or the hospital may also include a billing department subsystem 40068. The billing department subsystem 40068 may store and/or manage billing data associated with a respective department, such as the ER department 40070, colorectal department 40078, bariatric department 40072, and/or thoracic department 40066.

An edge tier system 40054 may be associated with a medical facility or a hospital and may include one or more edge computing systems 40064, for example. An edge computing system 40064 may include a storage sub-system and a server sub-system. In an example, the edge computing system comprising an edge server and/or a storage unit may provide additional processing and/or storage services to a surgical hub that is part of one of the departmental ORs (e.g., OR1 and OR2 of the colorectal department).

The surgical specific sub-network tier system 40052 and the edge tier system 40054 may be located within a Health Insurance Portability and Accountability Act (HIPAA)

boundary 40062. The surgical specific sub-network system 40052 and the edge tier system 40054 may be connected to the same local data network. The local data network may be a local data network of a medical facility or a hospital. The local data network may be within the HIPAA boundary. Because the surgical specific sub-network tier system 40052 and the edge tier system 40054 are located within the HIPAA boundary 40062, patient data between an edge computing system 40064 and a device located within one of the entities of the surgical specific sub-network tier system 40052 may flow without redaction and/or encryption. For example, patient data between an edge computing system 40064 and a surgical hub located in OR1 40074 of the colorectal department 40078 may flow without redaction and/or encryption.

The cloud tier system 40056 may include an enterprise cloud system 40060 and a public cloud system 40058. For example, the enterprise cloud system 40060 may be a cloud computing system 20008 that includes a remote cloud server sub-system and/or a remote cloud storage subsystem, as described in FIG. 1A. The enterprise cloud system 40060 may be managed by an organization, such as a private company. The enterprise cloud system 40060 may be in communication with one or more entities (e.g., edge computing systems 40064, surgical hubs located in ORs (e.g., OR1 40074) of the various departments (e.g., colorectal department 40078)) that are located within the HIPAA boundary 40062.

The public cloud system 40058 may be operated by a cloud computing service provider. For example, the cloud computing service provider may provide storage services and/or computing services to a plurality of enterprise cloud systems (e.g., enterprise cloud system 40060).

Figure 1C:
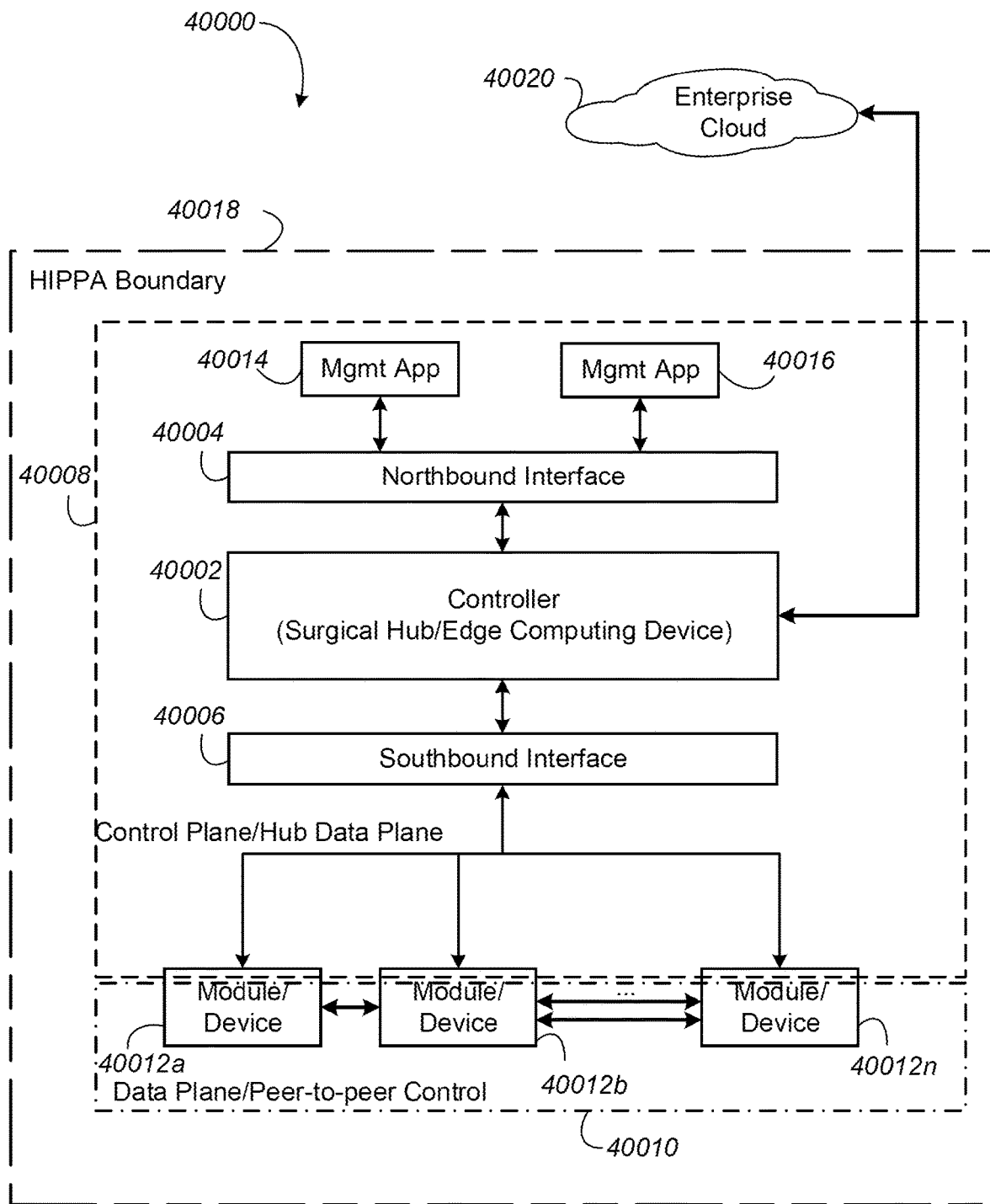
FIG. 1C is a logical diagram illustrating control plane and data plane of a surgical system.

FIG. 1C is a logical block diagram 40000 illustrating various communication planes in a surgical system. As illustrated in FIG. 1C, the communication planes between a controller 40002 and management applications 40014 and 40016 on one side and, the system modules and/or modular devices 40012a through 40012n on the other side, may use control plane 40008 and data plane 40010. In an example, in addition to the control plane 40008, a data plane may also exist between the system modules and/or modular devices 40012a through 40012n and the surgical hub. The data plane 40010 may provide redundant data plane paths (e.g., redundant data plane paths) between the system modules and/or the modular devices 40012a through 40012n that are associated with one or more surgical hubs. A surgical hub or one of the surgical hubs (e.g., in case of a plurality of surgical hubs present in an operating room) may act as a controller 40002. In an example, the controller 40002 may be an edge computing system that may reside within a Health Insurance Portability and Accountability Act (HIPAA) boundary where the surgical system is located, for example, as illustrated in FIG. 1B. The controller 40002 may be in communication with an enterprise cloud system 40020. As illustrated in FIG. 1C, the enterprise cloud system 40020 may be located outside the HIPAA boundary 40018. Accordingly, the patient data flowing to and/or from the enterprise cloud system 40020 may be redacted and/or encrypted.

The controller 40002 may be configured to provide a northbound interface 40004 and a southbound interface 40006. The northbound interface 40004 may be used for providing a control plane 40008. The control plane 40008 may include one or more management applications 40014 and 40016 that may enable a user to configure and/or manage system modules and/or modular devices modular devices 40012a through 40012n associated with a surgical system. The management applications 40014 and 40016 may be used to obtain status of various system modules and/or the modular devices 40012a through 40012n.

The management applications 40014 and 40016 using the control plane may interact with the controller 40002, for example, using a set of application programming interface (API) calls. The management applications 40014 and 40016 may interact with the controller 40002 via a management protocol or an application layer protocol to configure and/or monitor the status of a system module and/or a modular device. The management protocols or the application layer protocols used to monitor the status and/or configure a system module or a modular device associated with a surgical system may include the simple network management protocol (SNMP), TELNET protocol, secure shell (SSH) protocol, network configuration protocol (NETCONF), etc.

SNMP or a similar protocol may be used to collect status information and/or send configuration related data (e.g., configuration related control programs) associated with system modules and/or modular devices to the controller. SNMP or a similar protocol may collect information by selecting devices associated with a surgical system from a central network management console using messages (e.g., SNMP messages). The messages may be sent and/or received at fixed or random intervals. The messages may include Get messages and Set messages. The Get messages or messages similar to the Get messages may be used for obtaining information from a system module or a modular device associated with a surgical system. The Set message or messages similar to the Set message may be used for changing a configuration associated with a system module or a modular device associated with a surgical system.

For example, the Get messages or similar messages may include the SNMP messages GetRequest, GetNextRequest, or GetBulkRequest. The Set messages may include SNMP SetRequest message. The GetRequest, GetNextRequest, GetBulkRequest messages or similar messages may be used by a configuration manager (e.g., an SNMP manager) running on the controller 40002. The configuration manager may be in communication with a communication agent (e.g., an SNMP agent) that may be a part of a system module and/or a modular device in a surgical system. The SNMP message SetRequest message or similar may be used by the communication manager on the controller 40002 to set the value of a parameter or an object instance in the communication agent on a system module and/or a modular device of a surgical system. In an example, SNMP modules, for example, may be used to establish communication path between system modules and/or modular devices associated with a surgical system.

Based on the query or configuration related messages received from a management application, such as management applications 40014 and 40016, the controller 40002 may generate configuration queries and/or configuration data for querying or configuring the system modules and/or the modular devices associated with the surgical hub or the surgical system. A surgical hub (e.g., the surgical hub 20006 shown in FIG. 1A) or an edge computing system (e.g., the edge computing system 40064 shown in FIG. 1B) may manage and/or control various system modules and/or modular devices 40012a through 40012n associated with a surgical system. For example, the northbound interface 40004 of the controller 40002 may be used for changing control interactions between one or more modules associated and/or devices associated with a surgical system. In an example, the controller 40002 may be used for establishing one or more communication data paths between a plurality of modules and/or devices associated with a surgical system. The controller 40002 may use its southbound interface 40006 to send the control programs comprising queries and/or configuration changes to the system modules and/or the modular devices of the surgical system.

The system modules and/or the modular devices 40012a through 40012n of a surgical system, or the communication agents that may be a part of the system modules and/or the modular devices, may send notification messages or traps to the controller 40002. The controller may forward the notification messages or traps via its northbound interface 40004 to the management application 40014 and 40016 for displaying on a display. In an example, the controller 40002 may send the notification to other system modules and/or modular devices 40012a through 40012n that are part of the surgical system.

The system modules and/or the modular devices 40012a through 40012n of a surgical system or the communication agents that are part of the system modules and/or the modular devices may send responses to the queries received from the controller 40002. For example, a communication agent that may be part of a system module or a modular device may send a response message in response to a Get or a Set message or messages similar to the Get or the Set messages received from the controller 40002. In an example, in response to a Get message or a similar message received from the controller 40002, the response message from the system module or the modular device 40012a through 40012n may include the data requested. In an example, in response to a Set message or a similar message received from a system module or a modular device 40012a through 40012n, the response message from the controller 40002 may include the newly set value as confirmation that the value has been set.

A trap or a notification message or a message similar to the trap or the notification message may be used by a system module or a modular device 40012a through 40012n to provide information about events associated with the system modules or the modular devices. For example, a trap or a notification message may be sent from a system module or a modular device 40012a through 40012n to the controller 40002 indicating a status of a communication interface (e.g., whether it available or unavailable for communication). The controller 40002 may send a receipt of the trap message back to the system module or the modular device 40012a through 40012n (e.g., to the agent on the system module or a modular device).

In an example, TELNET protocol may be used to provide a bidirectional interactive text-oriented communication facility between system modules and/or modular devices 40012a through 40012n and the controller 40002. TELNET protocol may be used to collect status information and/or send configuration data (e.g., control programs) from/to the controller 40002. TELNET may be used by one of the management applications 40014 or 40016 to establish a connection with the controller 40002 using the transmission control protocol port number 23.

In an example, SSH, a cryptographic encrypted protocol, may be used to allow remote login and to collect status information and/or send configuration data about system modules and/or modular devices 40012a through 40012n from/to the controller 40002. SSH may be used by one of the management applications 40014 or 40016 to establish an encrypted connection with the controller 40002 using the transmission control protocol port number 22.

In an example, NETCONF may be used to perform management functions by invoking remote procedure calls using, for example, <rpc>, <rpc-reply>, or <edit-config> operations. The <rpc> and <rpc-reply> procedure calls or similar procedure calls may be used for exchanging information from a system module and/or a modular device associated with a surgical system. The NETCONF <edit-config> operation or a similar operation may be used for configuring the system modules and/or the modular devices associated with the surgical system.

The controller 40002 may configure the system modules and/or modular device 40012a through 40012n to establish a data plane 40010. The data plane 40010 (e.g., also referred to as a user plane or a forwarding plane) may enable a communication data path between a plurality of system modules and/or modular device 40012a through 40012n. The data plane 40010 may be utilized by the system modules and/or the modular device 40012a through 40012n for communicating data flows of data between the system modules and/or modular devices associated with a surgical system. The data flows may be established using one or more dedicated communication interfaces between the system modules and/or the modular devices associated with one or more surgical hubs of a surgical system. In an example, the data flows may be established over one or more local area networks (LANs) and one or more wide area networks (WANs), such as the Internet.

In an example, the data plane 40010 may provide support for establishing a first and a second independent, disjointed, concurrent, and redundant communication path for data flow between the system modules and/or modular devices 40012b and 40012n. As illustrated in FIG. 1C, redundant communication paths may be established between system modules/modular devices 40012b and 40012n. The redundant communication paths may carry same/redundant data flows between the system modules and/or modular devices. In an example, when or if some of the data packets are dropped on one of the redundant communication paths due to problems with one of the communication interfaces on the system modules/modular devices 40012b and 40012n, the system modules and/or the modular devices may continue to send/receive at least one copy of the dropped data packets over the second communication path.

Figure 2:
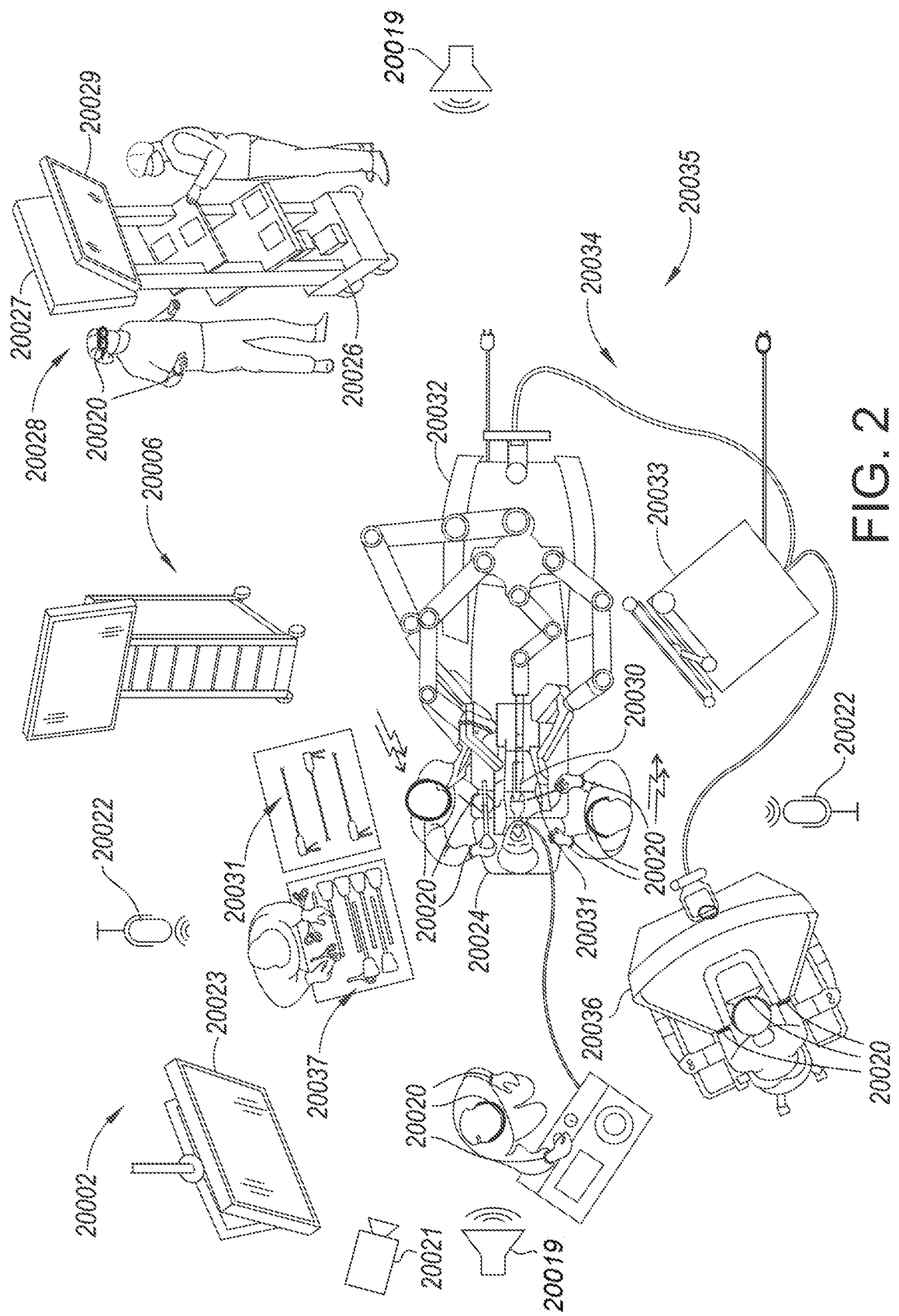
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1A. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1A may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
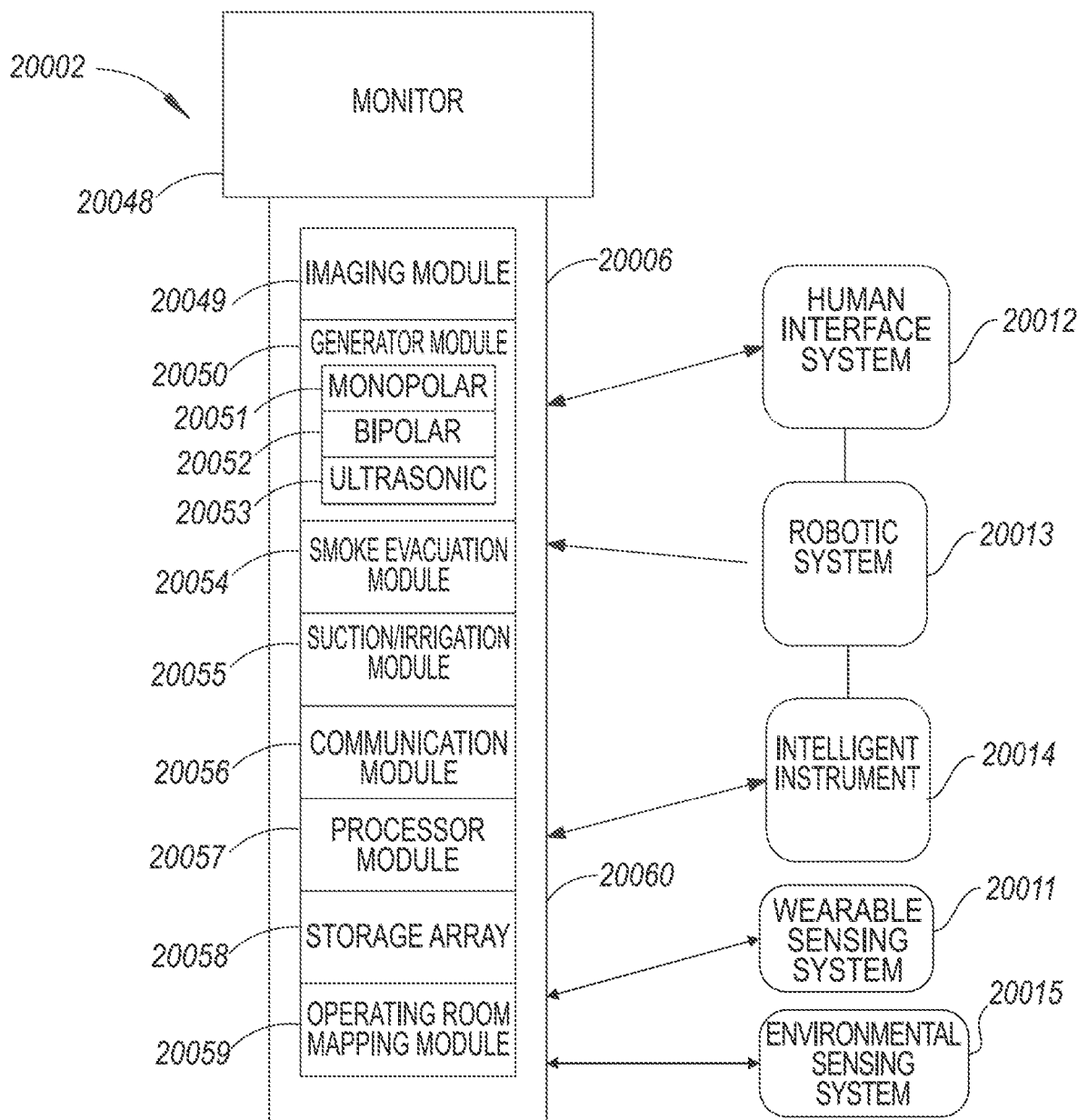
FIG. 3 illustrates an example surgical hub paired with various systems.

FIG. 3 shows an example surgical system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
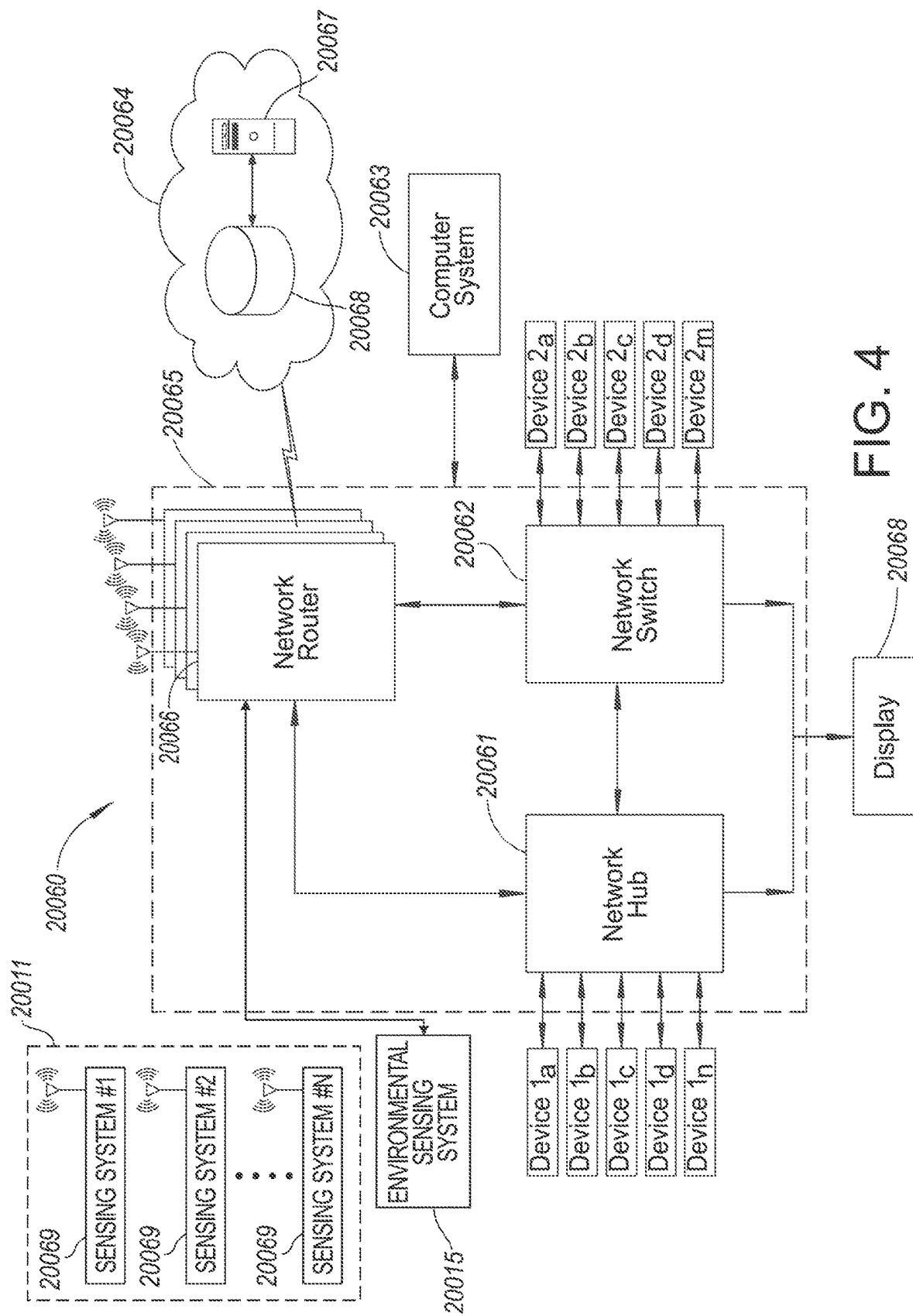
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
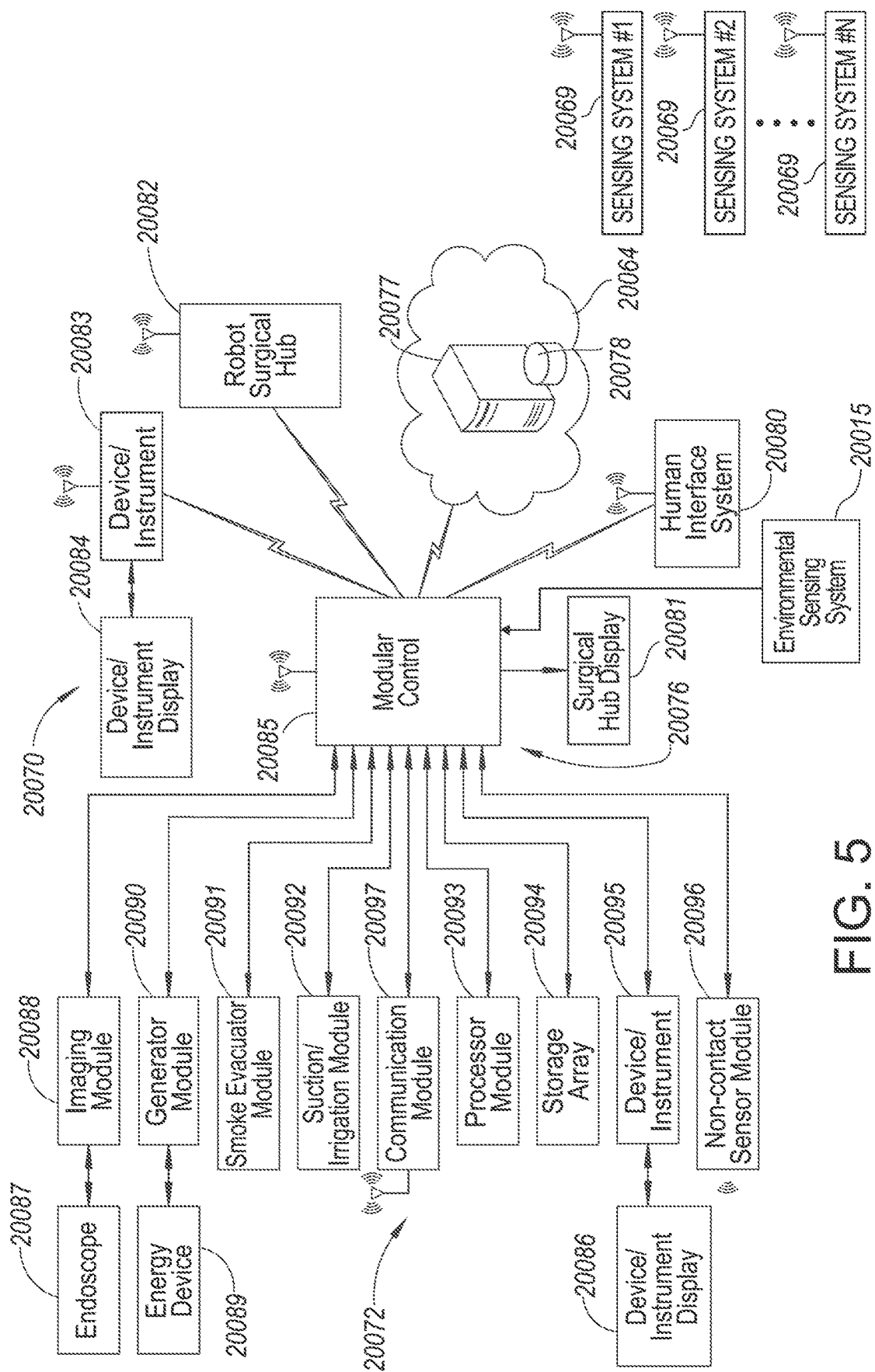
FIG. 5 illustrates an example computer-implemented interactive surgical system that may be part of a surgical system.

FIG. 5 illustrates a computer-implemented interactive surgical system 20070 that may be a part of the Surgical system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the Surgical systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control 20085 connected to multiple operating theater devices such as sensing systems 20001, intelligent surgical instruments, robots, and other computerized devices located in the operating theater.

As illustrated in the example of FIG. 5, the modular control 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control 20085 may also be in communication with one or more sensing systems 20069 and an environmental sensing system 20015. The sensing systems 20069 may be connected to the modular control 20085 either directly via a router or via the communication module 20097. The operating theater devices may be coupled to cloud computing resources and data storage via the modular control 20085. A robot surgical hub 20082 also may be connected to the modular control 20085 and to the cloud computing resources. The devices/instruments 20095 or 20084, human interface system 20080, among others, may be coupled to the modular control 20085 via wired or wireless communication standards or protocols, as described herein. The human interface system 20080 may include a display sub-system and a notification sub-system. The modular control 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control 20085 in conjunction with images and overlaid images.

Figure 6:
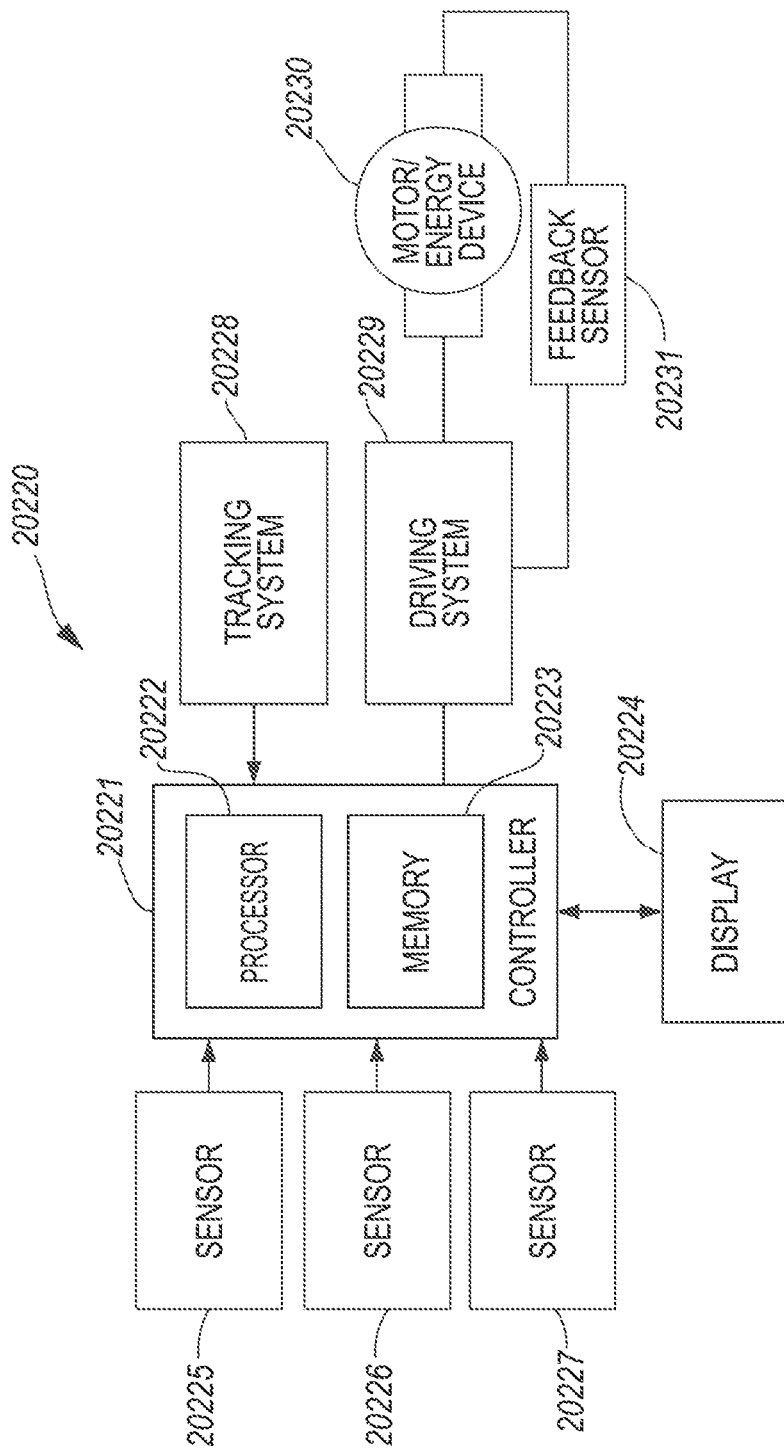
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
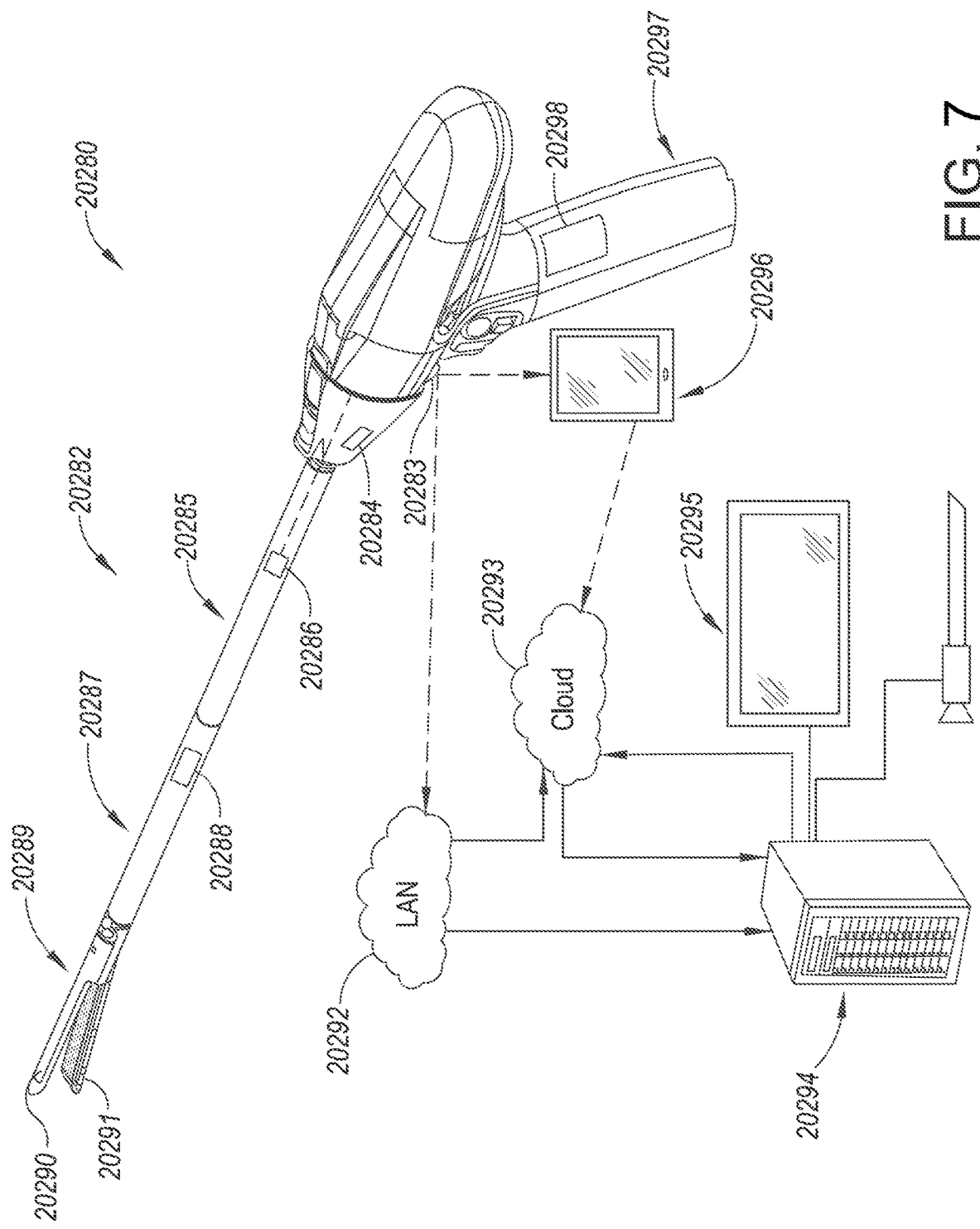
FIG. 7 shows an example surgical system that includes a handle having a controller and a motor, an adapter releasably coupled to the handle, and a loading unit releasably coupled to the adapter.

FIG. 7 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 8:
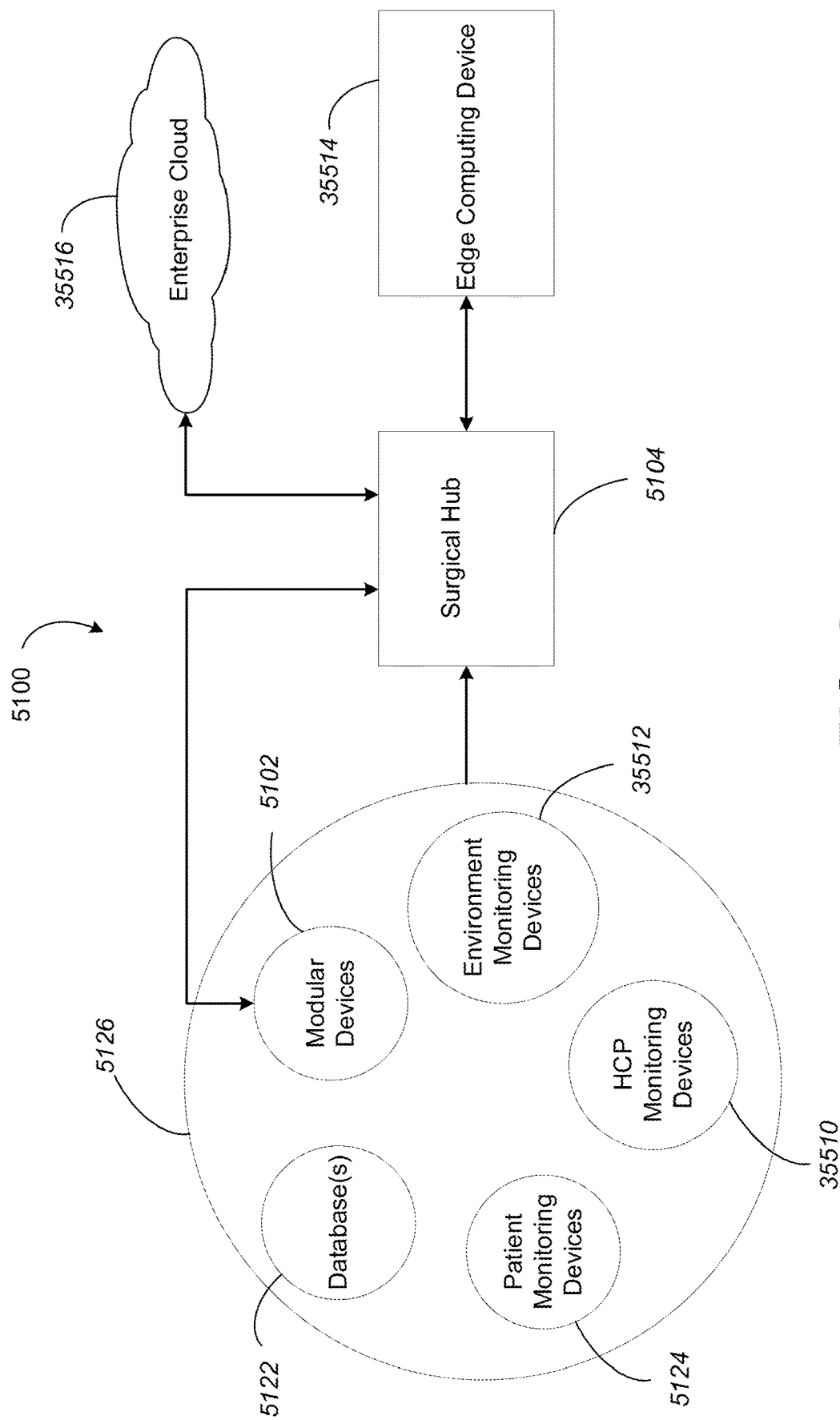
FIG. 8 shows an example situationally aware surgical system.

FIG. 8 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

A computing system may use redundant communication pathways for communicating surgical imaging feed(s). For example, surgical video feed may be sent via multiple video stream pathways to improve resilience of the feed.

Examples described herein monitor power utilization, needs, and inlet capacities to balance the distribution of power to coupled modules. A surgical power device may monitor the inlet power capacity from one or more sources. The surgical power device may balance power expectations of surgical modules with the available amount of operating room power to determine the amount of power that is distributed to each of the modules. The power expectations of the surgical modules may be based on provided forecasts of power needs, historic uses of specific surgical procedures, or prioritization of the surgical system needs. The power expectations of each of the surgical modules may cause the surgical power device to throttle the needs of each of the surgical modules. In examples, the surgical power device may restrict an amount of power to a surgical module if allowing that amount of power would be above the available amount of operating room power (e.g., the threshold operating room power). The available amount of operating room power may be a combination of inlet power as well as stored power within the operating room available to the surgical power device.

Figure 9A:
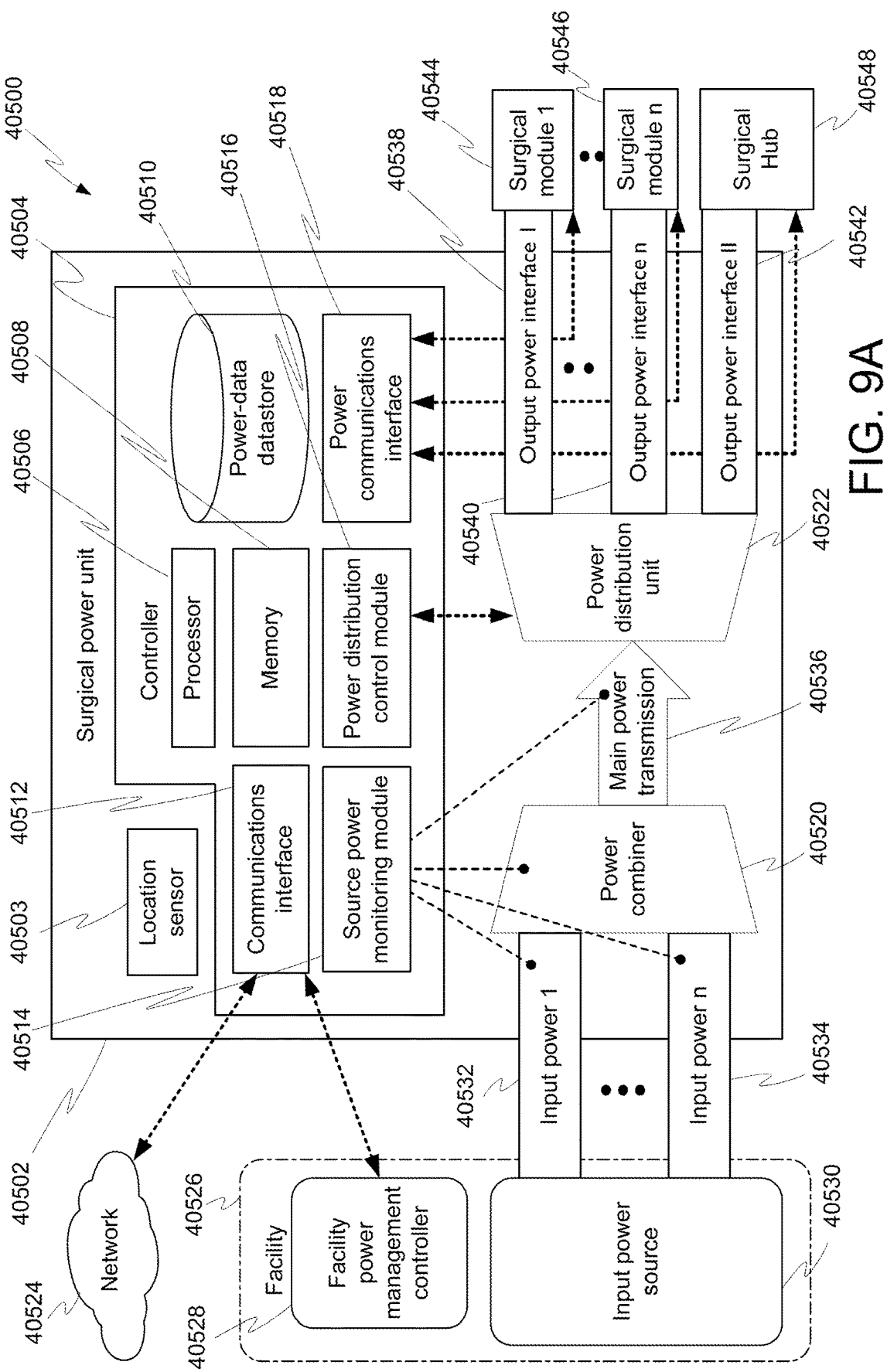
FIG. 9A shows an example of a surgical system that distributes and balances power.

FIG. 9A shows an example of a surgical system 40500 that distributes and balances power. The surgical system 40500 may include a surgical power unit 40502. The surgical power unit 40502 may include a location sensor 40503 and a controller 40504. The controller 40504 may include a processor 40506, a memory 40508, a power-data datastore 40510, a communications interface 40512, a source power monitoring module 40514, a power distribution control module 40516, and a power communications interface 40518. The surgical power unit 40502 may (e.g., may also) include a power combiner 40520 and a power distribution unit 40522.

The communications interface 40512 may communicate a with a surgical network 40524 and a power facility 40526. The power facility 40526 may include a facility power management controller 40528 and an input power source 40530. The input power source 40530 may provide input power 40532, 40534 to the power combiner 40520. The power combiner 40520 may combine the input power 40532, 40534 to provide a main power transmission 40536 to the power distribution unit 40522. The source power monitoring module 40514 may monitor the input power 40352, 40534, the power combiner 40520, and the main power transmission 40536.

The power distribution unit 40522 may include output power interfaces 40538, 40540, and 40542. Output power interfaces 40538, 40540 may interface with and provide output power to surgical modules 40544, 40546 and the output power interface 40542 may interface with and provide output power surgical hub 40548. The power distribution control module 40518 may communicate with the power distribution unit 40522. The power communications interface 40518 may communicate with the surgical modules 40544, 40546 and surgical hub 40548. The surgical modules 40544, 40546 may include any number of surgical modules, although two are shown in FIG. 9, with 40546 labeled "surgical module n" to indicate there may be any number of surgical modules in the surgical system 40500. Each of the surgical modules 40544, 40546 may have power expectations. In examples, the power distribution unit 40522 may be configured to receive the input power 40532, 40534 (e.g., the operating room power). The power distribution unit 40522 may provide portions of the operating room power to each of the output power interfaces 40538, 40540.

Figure 9B:
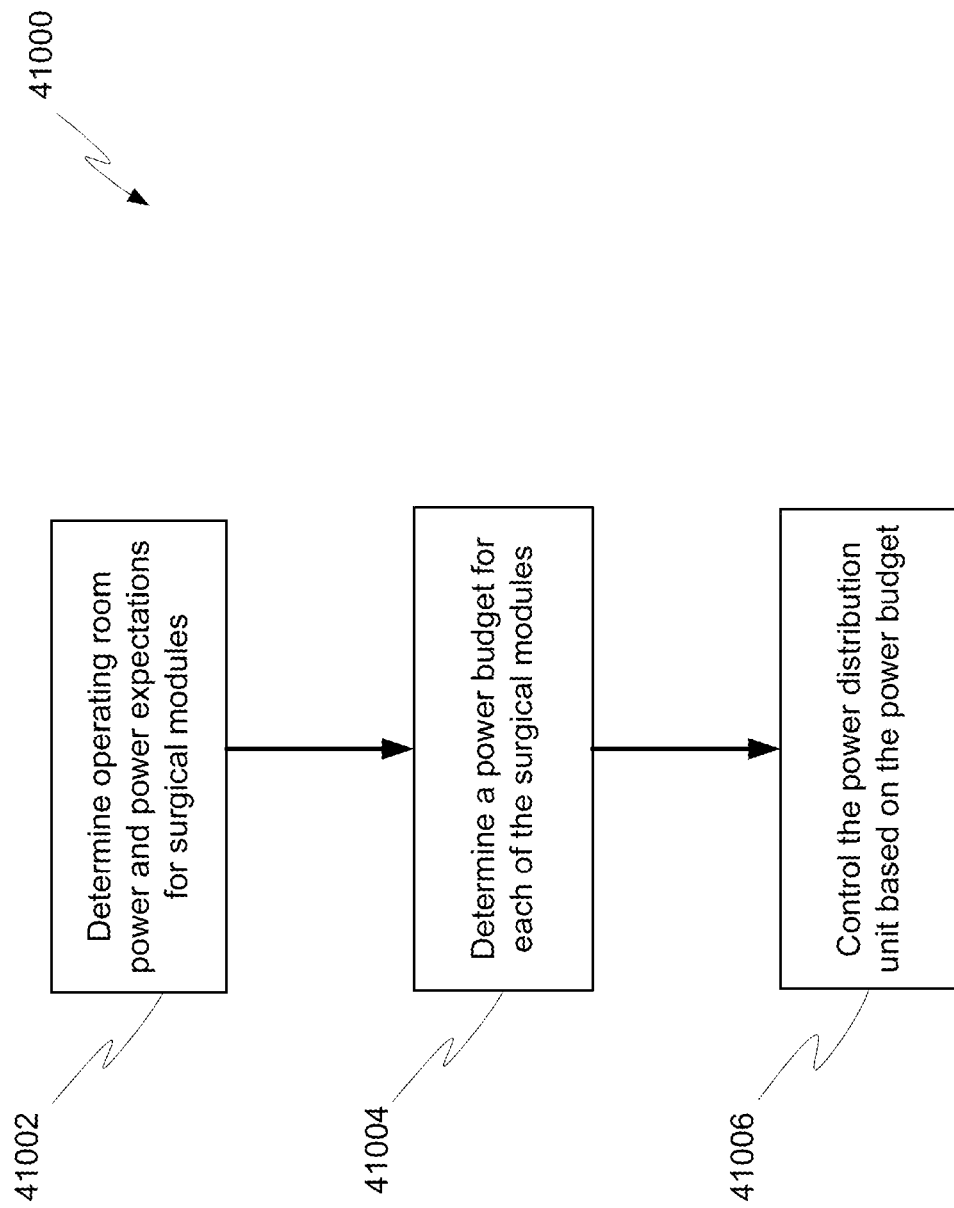
FIG. 9B shows an example flow chart for distributing and balancing power.

FIG. 9B shows an example flow chart 41000 for distributing and balancing power. At 41002, the power distribution control module 40518 of the controller 40504 may determine the amount of operating room power and each of the power expectations of each of the surgical modules 40544, 40546. At 41004, the power distribution control module 40518 of the controller 40504 may determine a power budget for each of the surgical modules 40544, 40546 based on the available amount of operating room power and each of the power expectations of each of the surgical modules 40544, 40546 determined at 41002. At 41006, the power distribution control module 40518 of the controller 40504 may control the power distribution unit 40522, based on the power budget determined at 41002, to set each of the portions of the operating room power to each of the output power interfaces 40538, 40540.

In examples, the power distribution control module 40518 of the controller 40504 may learn each of the surgical module types of each of the surgical modules 40544, 40546. The surgical module types may be a smoke evacuator, a visualization system, a generator, a header, a monitoring or imaging system, or an insufflation system. The power distribution control 40518 of the controller 40504 may set a prioritization of each of the surgical modules 40544, 40546 based on the surgical module types. Based on the prioritization of each of the surgical modules 40544, 40546, the power distribution control module 40518 of the controller 40504 may be determined for each of the surgical modules 40544, 40546. In examples, the prioritization of the surgical modules 40544, 40546 may be received directly from the surgical modules 40544, 40546. In examples, the prioritization of the surgical modules 40544, 40546 may be received from the surgical hub 40548. Each of the output power interfaces 40538, 40540, 40542 may have their own power prioritizations (e.g., a first output power interface may have a first power prioritization, etc.).

Figure 10:
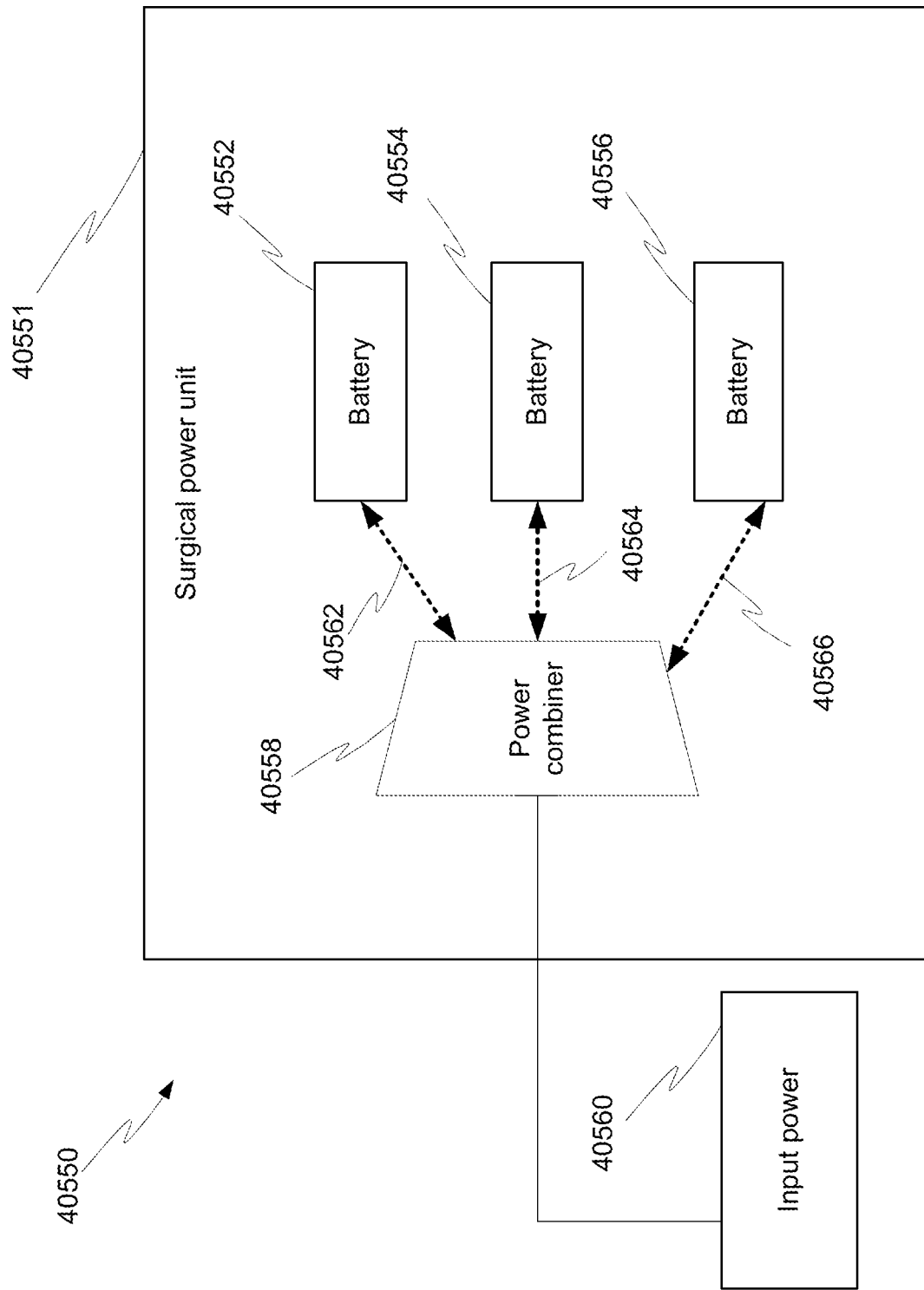
FIG. 10 shows an example of a surgical system that distributes and balances power with supplemental batteries.

FIG. 10 shows an example of a surgical system 40550 that distributes and balances power with supplemental batteries. The surgical system 40550 may include a surgical power unit 40551. The surgical power unit 40551 may include batteries 40552, 40554, 40556 that may act to balance the surgical modules 40544, 40546 (shown in FIG. 9) and surgical hub 40548 (shown in FIG. 9) power peak needs. The batteries 40552, 40554, 40556 may buffer the inlet power 40560 and may communicate with the power combiner 40558 via communication lines 40562, 40564, 40566 to increase overall power capacity and utilization. The inlet power 40560 may include alternating current (AC) power sources and/or direct current (DC) power sources. The batteries 40552, 40554, 40556 may include supplemental battery storage of energy to accommodate peak outputs. The batteries 40552, 40554, 40556 may enable the surgical system 40550 to accommodate short term peaks in the supplied power without overloading a continuous current maximum fuse or breaker. The batteries 40552, 40554, 40556 may power the surgical system 40558 for minutes or hours without direct power from the inlet power 40560. In examples, the batteries 40552, 40554, 40556 may be programmed to recharge themselves in a down procedure time or if they sense the operating room is in a dormant or low need condition.

Figure 11:
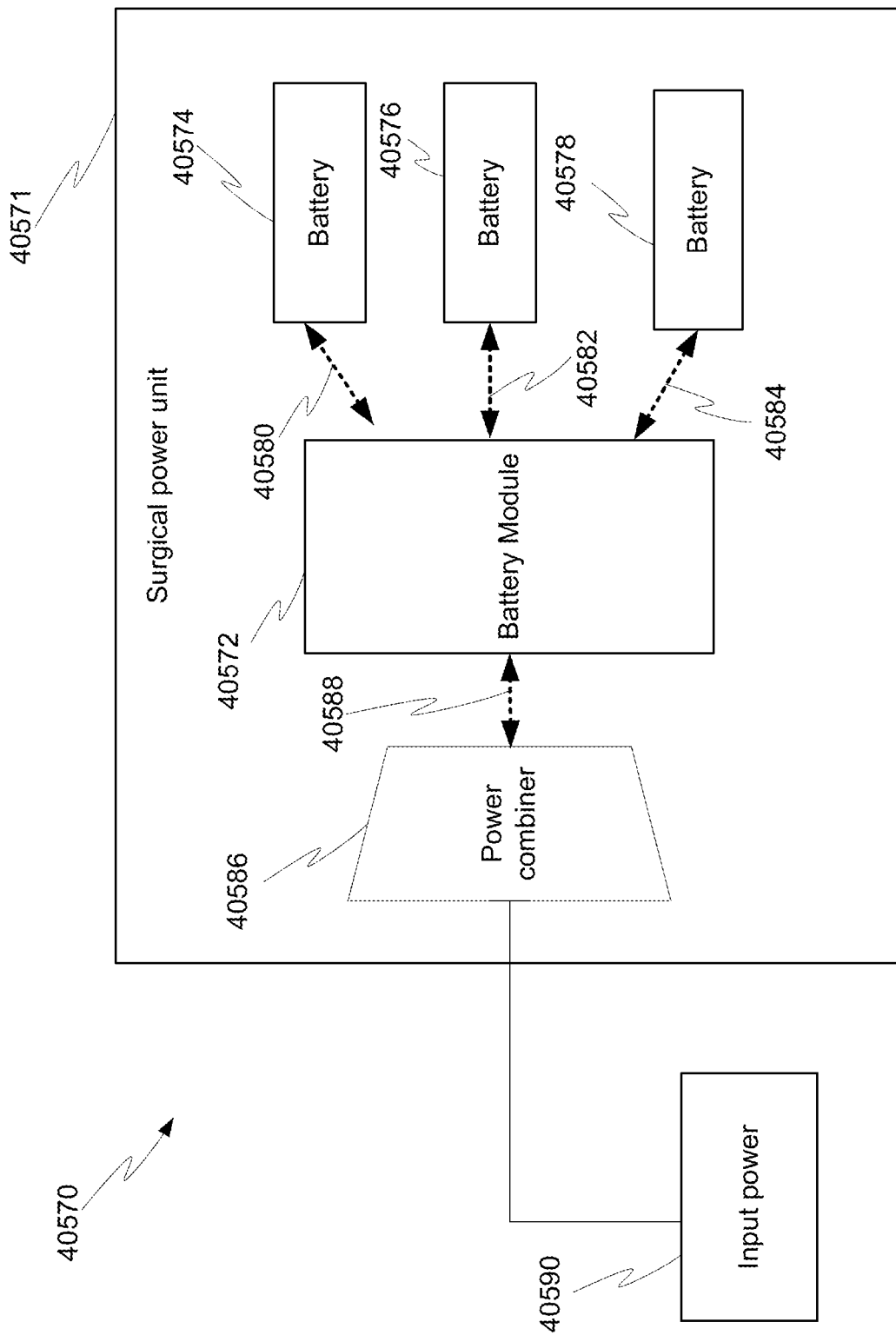
FIG. 11 shows an example of a surgical system that distributes and balances power with an integrated battery module.

FIG. 11 shows an example of a surgical system 40570 that distributes and balances power with an integrated battery module. The surgical system 40570 may include a surgical power unit 40571. The surgical power unit 40571 may include an integrated pass thru battery module 40572 that communicates with batteries 40574, 40576, 40578 via communication lines 40580, 40582, 40584 and the power combiner 40586 via communication line 40588. The integrated pass thru battery module 40572 may act as an uninterruptible power supply, a spike and through filter. The integrated pass thru battery module 40572 may accommodate power needs or peak output needs that may exceed the input power 40590 supplied to the power combiner within the operating room.

In examples, the surgical power unit 40502 (as shown in FIG. 9) may be capable of switching power coupling between the input power from the inlet power source 40530 to balance the load within power distribution unit 40522.

The power distribution unit 40522 may include the output power interfaces 40538, 40540, 40542 which may be plugged to the surgical modules 40544, 40546 and the surgical hub 40548. The power distribution unit 40522 may be capable of switching and balancing the power between the surgical modules 40544, 40546 and the surgical hub 40548. The power distribution unit 40522 may use an anticipation algorithm that may estimate the needs of the surgical modules 40544, 40546 and the surgical hub 40548 for upcoming aspects of the procedures. The power distribution unit 40522 may pre-balance power to the surgical modules 40544, 40546 and the surgical hub 40548 in such a manner to anticipate peak output conditions.

The surgical power unit 40502 may provide smart metering of power into the surgical hub 40548 and may utilize the attached surgical modules 40544, 40546 to balance the needs of the surgical modules 40544, 40546. The surgical power unit 40502 may record the power usage throughout the procedures and from one procedure to the next to learn the power utilization. The surgical power unit 40502 may store the power usage information within the power data datastore 40510. The surgical power unit 40502 may attach metadata, such as metadata of procedure type, surgeon, complications, or instrument utilization to decide the power distribution profiles of the surgical module 40544, 40546 combinations during certain surgical procedures. The power distribution profiles may be sent to the power distribution unit 40522 from the power distribution control module 40516 within the surgical power unit 40502. The power distribution profiles may be reconfigured to minimize the maximum power usage in peak need situations or overall average power usage. The power distribution profiles may (e.g., may also) be used as a proxy for the heat generation of the surgical modules 40544, 40546 and may help prevent overheating. Accumulated data for power usage may be used to predict peak usages for different surgical procedures using a different combination of the surgical modules 40544, 40546. The accumulated data may be used to communicate the need to lower the power needs of the surgical modules 40544, 40546 in anticipation of an upcoming peak power usage of a different surgical module.

As the surgical system 40500 approaches the maximum current condition, the surgical power unit 40502 may utilize a prioritization matrix to inform some of the surgical modules 40544, 40546 to limit their power needs to accommodate other higher priority surgical modules 40544, 40546 or tasks. In examples, the surgical power unit 40502 may throttle the current to some of surgical modules 40544, 40546, thereby not supplying the restricted surgical modules 40544, 40546 with all the current they could use.

In examples, one of the surgical modules 40544, 40546 may be an advanced visualization system and one of the surgical modules 40544, 40546 may be a smoke evacuator. The advanced visualization system may increase resolution, processing, or multi-spectral sources above the normal envelope it uses. The surgical power unit 40502 may inform the surgical hub 40548 of its power needs and the surgical hub 40548 may require or throttle the power to the smoke evacuator compressor or blower motor to provide a buffer for the advanced visualization system, for example. The surgical hub 40502 may understand that the smoke evacuator could continue to operate with restricted power, but the advanced visualization system may not run at the needed resolution without the ability to exceed its normal power capacity.

In examples, other sensing systems within the operating room may ensure the throttled system does not prioritize its own system in relation to other critical systems. In examples, one of the surgical modules 40544, 40546 may be an insufflation system. The insufflation system may be one of the throttled systems to provide power to other critical systems. If in the throttled mode, the surgical hub 40548 monitors that the abdomen insufflation pressure drops below minimum acceptable conditions, the throttled system may be re-prioritized to eliminate the condition and then return to throttling or switch to throttling another system.

In examples, the surgical power unit 40502 may restrict power to some of the surgical modules 40544, 40546 to provide some of the other surgical modules 40544, 40546 more buffer, which may involve multiple modules and multiple restrictions or grants or differing magnitudes. In the event a power balance can not be reached, all of the surgical modules 40544, 40546 may be throttled to differing levels either automatically or by indicating to the user the issue and requesting guidance as to which systems require prioritization at which times during the procedure. The guidance may be used to make the same decisions in the future as automated reactions by learning the users needs and priorities for a given procedure.

In examples, some of the surgical modules 40544, 40546 may be supplied less power between uses, but may not be powered off, in order to minimize inrush current. Some of the surgical modules 40544, 40546 may be sequenced out of sync (e.g., slightly out of sync) of the power facility 40526. Some of the surgical modules 40544, 40546 may draw power beyond the operating room wiring capabilities. The input power 40532, 40534 may be throttled along with the current of certain modules (e.g., non-smart modules, such as the smoke evacuate module). The input power 40532, 40534 may be monitored for correlation to the output power from the output power interfaces 40538, 40540, and 40542 to adjust the thresholds of the initiation of force controls using the output power to linked systems. The inrush current and potential stepped draws may be detected. In examples, the idealization of the power utilization of equipment may be based on the startup power signature of the equipment. Startup voltage and current draw to identify a surgical system for interactive operating room usage may be utilized. Power management control may enable current draws and voltage needs beyond the standard inlet wiring capacity.

Examples described herein may relate to the intercommunication and cooperative operation between surgical modules. The intercommunication and cooperative operation may be based on the physical and communication connections between surgical modules.

Figure 12:
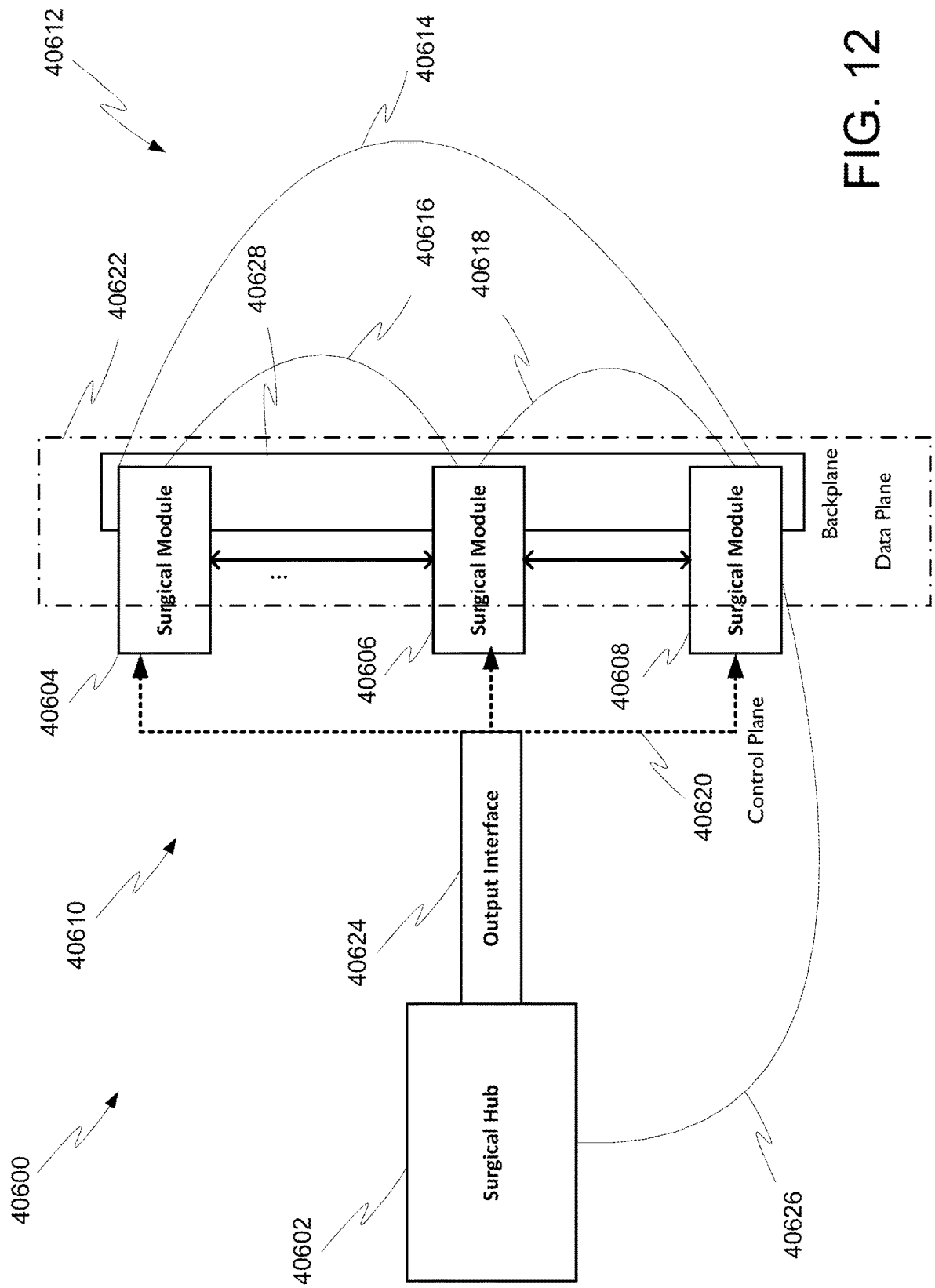
FIG. 12 shows an example of a surgical system with physical and communication connections between surgical modules and a surgical hub.

FIG. 12 shows an example of a surgical system 40600 with physical and communication connections between surgical modules and a surgical hub. The surgical system 40600 may include a surgical hub 40602 and surgical modules 40604, 40606, 40608. Although three surgical modules are shown in FIG. 12, the surgical system 40600 may include any number of surgical modules. Although one surgical hub 40602 is shown in FIG. 12, the surgical system 40600 may include multiple surgical hubs. The surgical hub 40602 may have the capacity for the surgical modules 40604, 40606, 40608 to be cumulatively coupled via a first port 40610 as well as directly coupled via a second port 40612 simultaneously. The interconnectivity of the surgical modules 40604, 40606, 40608 may enable some of the surgical modules 40604, 40606, 40608 to work cooperatively with the exclusion of some of the other surgical modules 40604, 40606, 40608 or receive data and control from multiple surgical modules 40604, 40606, 40608 simultaneously. The first port 40610 may include a control plane 40620, a data plane 40622, and a backplane 40628 that facilitate data communication between each of the surgical modules 40604, 40606, 40608 and the surgical hub 40602. The second port 40612 may be external wired connections 40614, 40616, 40618 connecting each of the surgical modules 40604, 40606, 40608 to each other separate from the first port 40610. The surgical hub 40602 may include an output interface 40624 that may interface with each of the surgical modules 40604, 40606, 40608. The connections between the surgical modules 40604, 40606, 40608 and the surgical hub 40602 may not be the same performance level. In examples, some of the connections between the surgical modules 40604, 40606, 40608 may provide redundant pathways of communication that may be used cooperatively. In examples, there may be daisy chain coupling of surgical modules 40604, 40606, 40608. There may be a coupling hierarchy based on critical functionality of certain surgical modules.

In examples, the surgical system 40600 may provide one-way monitoring communication for use in controlling aspects of another smart system. The surgical modules 40604, 40606, 40608 may be non-smart surgical modules, semi-smart surgical modules, smart surgical modules, and/or intelligent surgical modules, which is described in further detail below. The surgical system 40600 may provide integrated monitoring enabling non-smart surgical modules to be used with smart surgical modules. The integrated monitoring may include monitoring for the interference of non-smart surgical modules during the activation of smart surgical modules. This may prevent accidental simultaneous energy activation of non-smart surgical modules and smart surgical modules. In examples, the integrated monitoring may prevent a portion of the non-smart surgical modules and the smart surgical modules from activating simultaneously. For example, the ultrasonic advanced energy portion of a smart surgical module may be used in combination with a monopolar radio frequency application from another surgical module while preventing the smart surgical module's radio frequency portion to be used simultaneously with the monopolar radio frequency application. For example, the surgical module 40604 may be a non-smart surgical module and surgical module 40606 may be a smart surgical module. Each of the surgical modules 40604 and 40606 may work independently from one another or together during certain times of certain procedures. The smart module may incrementally control the non-smart module. In examples, the surgical modules 40604, 40606 may be a generator and smoke evacuator. The generator may a step electrical potential output to indicate the increase airflow, the activation of the energy device to increment the smoke evacuator, or the increase/decrease of speed without other cooperative communication.

Figure 13:
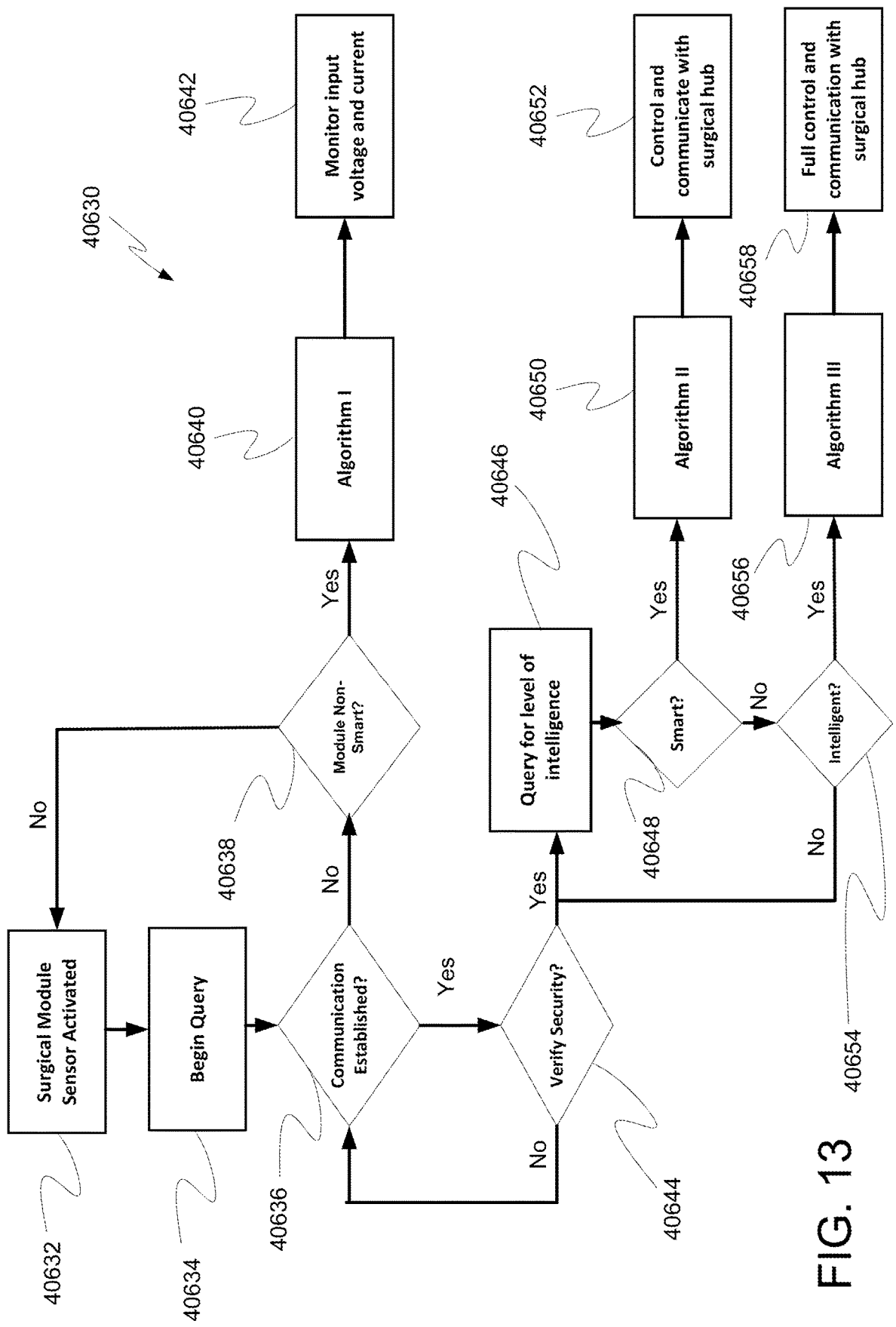
FIG. 13 shows an example of a flow chart of attaching a surgical module to an existing group of surgical modules.

FIG. 13 shows an example of a flow chart 40630 of attaching a surgical module to an existing group of surgical modules. The surgical module may in the form of a monopolar generator. At 40632, the surgical module sensor may be activated. At 40634, the surgical system may begin a query of the newly attached surgical module to establish communication with the existing surgical modules. The surgical system may be surgical system 40600 described in FIG. 12, but may be other surgical systems as well. At 40636, the surgical system may determine if communications are established. If no, then at 40638, the surgical system may determine if the surgical module is non-smart. If no, then the surgical module sensor may be activated again at 40632. If yes, then at 40640, a first algorithm may be performed by the surgical module. At 40642, the surgical module may monitor input voltage and current as performed by the first algorithm.

If communications are established at 40636, then at 40644, the surgical system may verify security. If security is not verified, then the surgical system may determine if communications are established again at 40636. If security is verified, then the surgical system may query for the level of intelligence the surgical module at 40646. At 40648, the surgical system may determine if the surgical module is smart. If yes at 40648, then at 40650, a second algorithm may be performed by the surgical module. At 40652, the surgical module may control and communication the surgical hub as performed by the second algorithm. If no at 40648, then at 40654, the surgical system may determine if the surgical module is intelligent. If no at 40654, then the surgical system may query for the level of the surgical module again at 40646. If yes at 40654, then at 40656, a third algorithm may be performed by the surgical module. At 40658, the surgical module may have full control and communication with the surgical hub as performed by the third algorithm.

Figure 14:
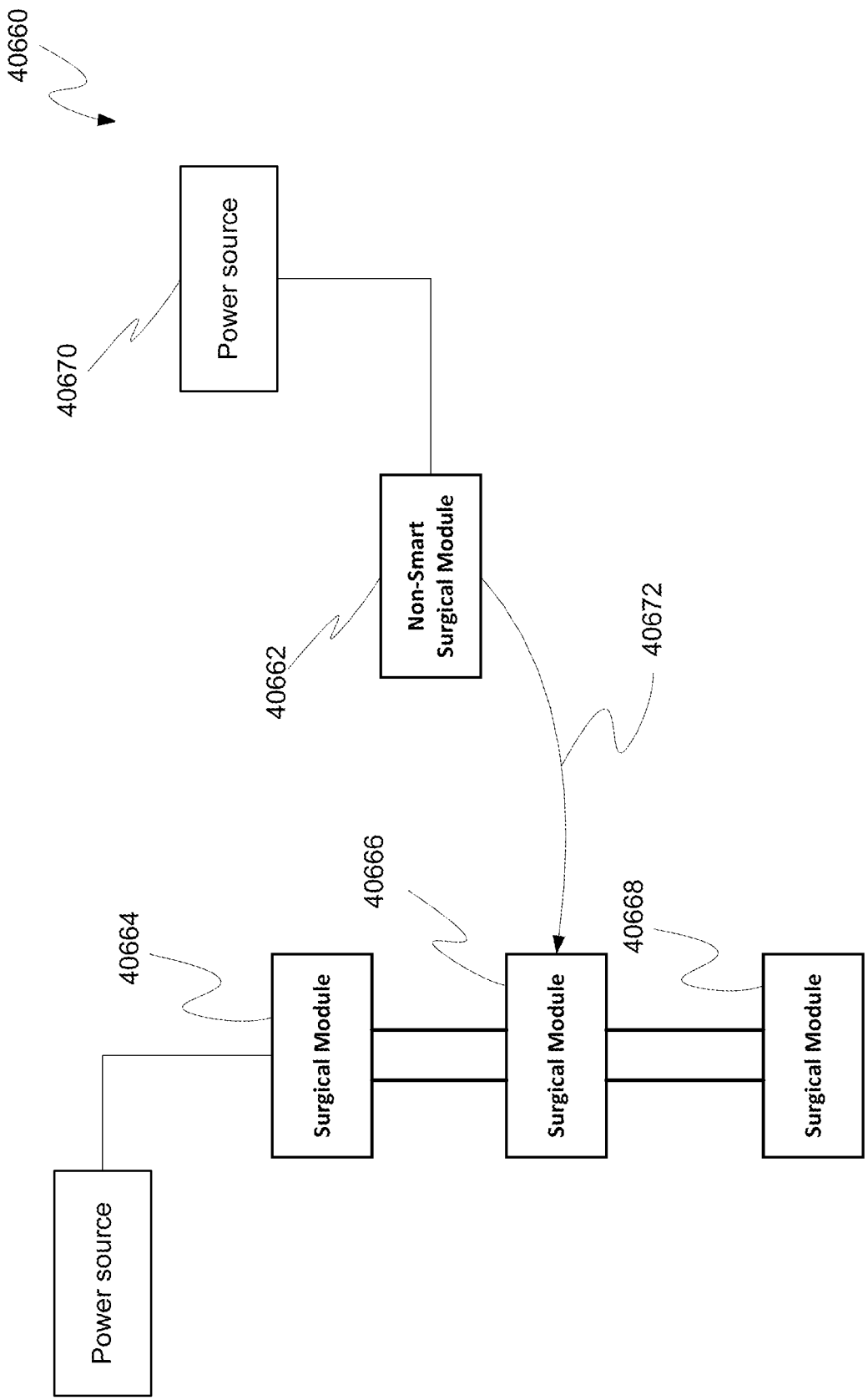
FIG. 14 shows an example of a surgical system with a non-smart surgical module.

FIG. 14 shows an example of a surgical system 40660 with a non-smart surgical module. The surgical system 40660 may include a non-smart surgical module 40662 attached to the surgical modules 40664, 40666, 40668. The non-smart surgical module 40662 may be power independent from the surgical modules 40664, 40666, 40668, having its own power source 40670. The non-smart module 40662 may have one way data flow 40672 with minimal communications with the surgical modules 40664, 40666, 40668.

Figure 15:
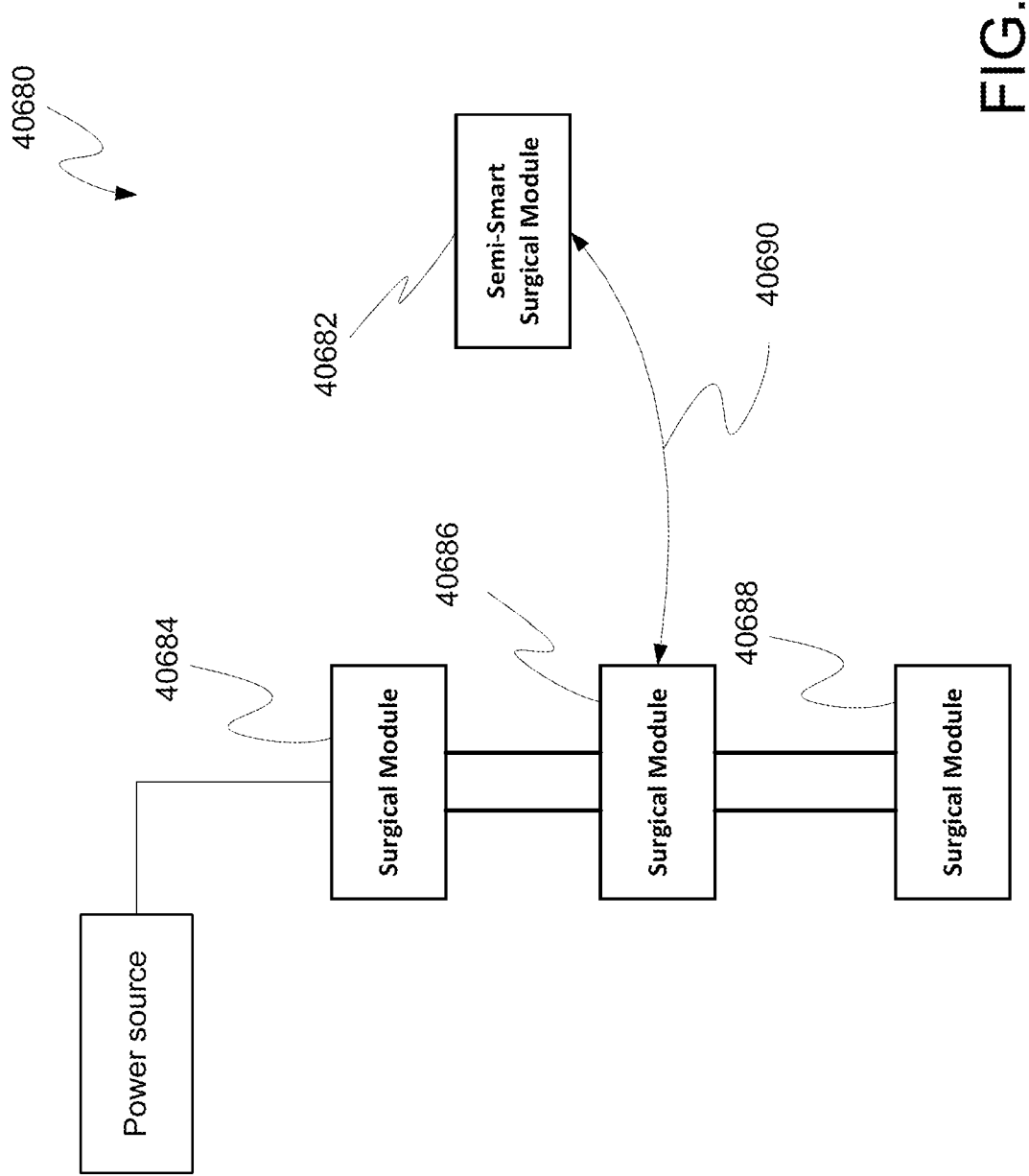
FIG. 15 shows an example of a surgical system with a semi-smart surgical module.

FIG. 15 shows an example of a surgical system 40680 with a semi-smart surgical module. The surgical system 40680 may include a semi-smart surgical module 40682 attached to the surgical modules 40684, 40686, 40688. The semi-smart surgical module 40682 may include two way communication 40690 with the surgical modules 40684, 40686, 40688. The semi-smart surgical module 40682 may monitor the input power. The semi-smart surgical module 40682 may have minimal command and control of its functions.

Figure 16:
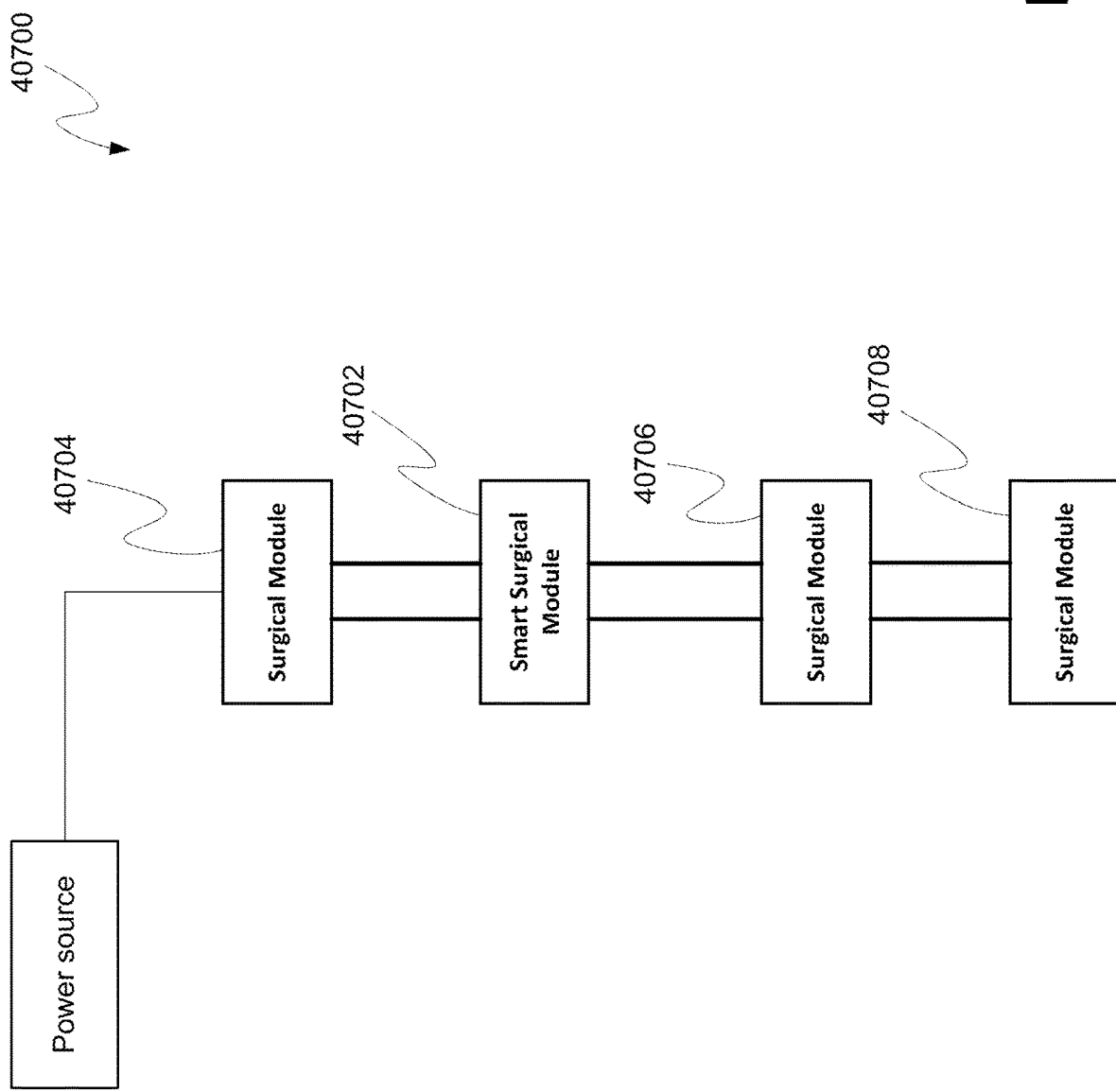
FIG. 16 shows an example of a surgical system with a smart surgical module.

FIG. 16 shows an example of a surgical system 40700 with a smart surgical module. The surgical system 40700 may include a smart surgical module 40702 attached to the surgical modules 40704, 40706, 40708. The smart surgical module 40702 may include two way communication with the surgical modules 40704, 40706, 40708, which may include a bipolar generator. The smart surgical module 40702 may have enhanced command and control of its functions. The smart surgical module 40702 may monitor its inputs and outputs.

In examples, the surgical systems described herein may include an intelligent surgical module. The intelligent surgical module may include multiple communication paths. The intelligent surgical module may have full command and control of its functions.

The surgical system 40600 (shown in FIG. 12) may include a configuration to a surgical hub port available when the surgical modules 40604, 40606, 40608 in communication with the surgical hub 40602 by sharing a bus. Each surgical module 40604, 40606, 40608 may have a specific identification. The surgical modules 40604, 40606, 40608 may be in close proximity to each other to align well with a serial protocol. In examples, the surgical system 40600 may be set up in a primary source/secondary source configuration. The surgical hub 40602 may be the primary source and the surgical modules 40604, 40606, 40608 may be the secondary sources. The surgical hub 40602 may be connected to the surgical modules 40604, 40606, 40608 via a first port 40610. The surgical modules 40604, 40606, 40608 may directly connect to each other via a second port 40612. Extra cables 40614, 40616, 40618 may allow data pass from the surgical modules 40604, 40606, 40608 and an optional cable 40626 may allow data to optionally pass from surgical modules 40604, 40606, 40608 to surgical hub 40602. In examples, data may pass to the surgical hub 40602 via the second port 40612. In examples, the data may not pass to the surgical hub 40602 via the second port 40612. Certain functions and data transfers may be isolated from the surgical hub 40602 via the second port 40612. Certain functions and data transfers may be communicated to the surgical hub 40602 via the first port 40610. In examples, the second port 40612 between each of the surgical modules 40604, 40606, 40608 may be an additional slow communication portal. In examples, the second port 40612 may include an auxiliary data path from a surgical module 40604, 40606, 40608 to the surgical hub 40602.

Figure 17:
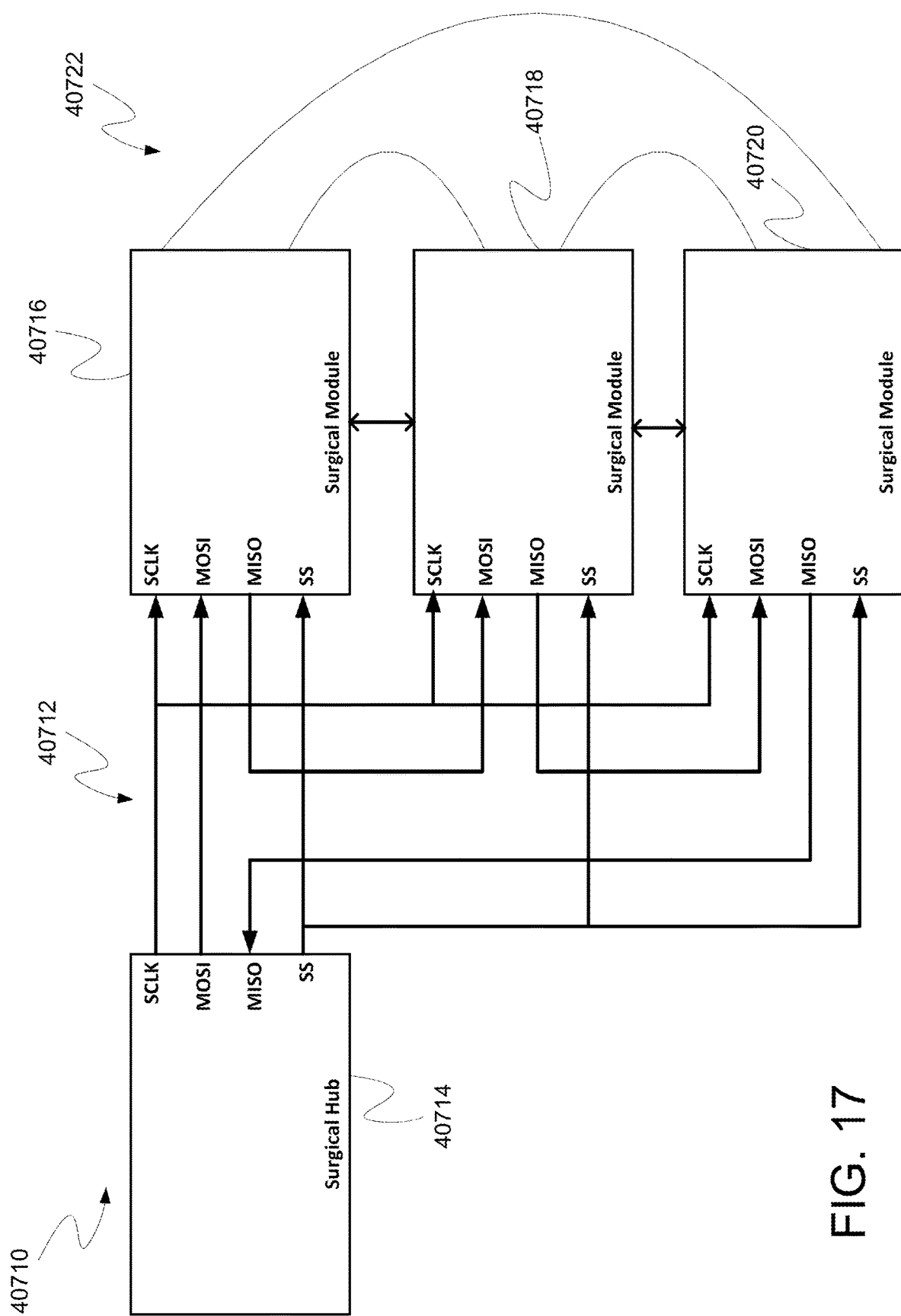
FIG. 17 shows an example of a surgical system with a SPI communication layout.

FIG. 17 shows an example of a surgical system 40710 with a SPI communication layout. In examples, the surgical system 40710 may be two independent communication paths. One communication pathway (e.g., the primary communication pathway) may be a SPI communication bus 40712 between the surgical hub 40714 and the surgical modules 40716, 40718, 40720. A secondary communication pathway 40722 (e.g., the secondary communication pathway) may be a surgical module to surgical module bus.

In examples, at least one of the surgical modules 40716, 40718, 40720 may be set up in a monopolar configuration and at least one of the surgical modules 40716, 40718, 40720 may be configured in a bipolar mode. If a surgeon picks up the monopolar device, the surgical hub 40710 may acknowledge this activity and ensure full input power is available for the at least one surgical module 40716, 40718, 40720 set up in a monopolar configuration. The surgical hub 40710 may alert the remaining surgical modules 40716, 40718, 40720 that the at least one surgical module 40716, 40718, 40720 set up in a monopolar configuration may be energized. For example, the at least one surgical module 40716, 40718, 40720 set up in a monopolar configuration may be a smoke evacuator and may acknowledge the information and begin to power up into idle mode. The at least one surgical module 40716, 40718, 40720 set up in a bipolar configuration may acknowledge this information and lock out any activation activity. The at least one surgical module 40716, 40718, 40720 set up in a monopolar configuration may receive a signal from the at least one surgical module 40716, 40718, 40720 set up in a bipolar configuration that the energizing switch has been depressed. In response, the at least one surgical module 40716, 40718, 40720 set up in a bipolar configuration may send a high speed status update to surgical module bus the secondary communication pathway 40722 while simultaneously alerting the surgical hub 40714 of the device change of state. The surgical modules 40716, 40718, 40720 may receive this high speed message and change their states. In examples, if the at least one surgical module 40716, 40718, 40720 set up in a monopolar configuration is a smoke evacuator module, it may spin up and begin pulling more smoke from the site. If the at least one surgical module 40716, 40718, 40720 set up in a bipolar configuration is an advanced visualization module, it may increase the intensity of the main light to compensate for the additional smoke in the field. The surgical hub 40714 may increase the input voltage to the remaining modules 40716, 40718, 40720 to compensate for the loss due to the at least one surgical module 40716,

40718, 40720 set up in a monopolar configuration. In examples, other communication pathways between a surgical hub and surgical modules may be a USB data connect, an Rs-232 dedicated interface, and/or a I2C interface.

As shown in FIG. 12, the surgical system 40600 may control the interrelationship between surgical modules 40604, 40606, 40608. In examples, the surgical modules 40604, 40606, 40608 may connect as a peer-to-peer network allowing some surgical modules 40604, 40606, 40608 to run completely autonomous to one another even when connected. In examples, there may be server-bus connection where if a surgical module 40604, 40606, 40608 is connected, the surgical module 40604, 40606, 40608 may surrender some or all of its control to the server module. The surgical modules 40604, 40606, 40608 may run separately from the surgical hub 40602 as an independent stand alone system and if connected to the surgical hub 40602, recognize the connect and adjust its autonomy to that of the surgical hub 40602.

In examples, each of the surgical modules 40604, 40606, 40608 within the surgical system 40600 may be connected via the first port 40610 to the surgical hub 40602. Each of the surgical modules 40604, 40606, 40608 may be connected via the second port 40612 to each other (e.g., each surgical module may be connected to at least one additional surgical module). Each of the surgical modules 40604, 40606, 40608 may have a controller (not shown) configured to receive surgical data. The controller of each of the surgical modules 40604, 40606, 40608 may determine if the surgical data is a first type of data or a second type of data. Based on the determination, the controller of each of the surgical modules 40604, 40606, 40608 may instruct each of the surgical modules 40604, 40606, 40608 to send the surgical data to the first port 40610 if the surgical data is the first type and to the second port 40612 if the surgical data is the second type. In examples, the second port 40612 may excluded from the surgical hub 40602. In examples, the second port 40612 may be included with the surgical hub 40602. Each of the surgical modules 40604, 40606, 40608 may be a non-smart surgical module, a semi-smart surgical module, or a smart surgical module. Each of the surgical modules 40604, 40606, 40608 may be a smoke evacuator, a visualization system, a generator, a header, a monitoring or imaging system, or an insufflation system.

Figure 18:
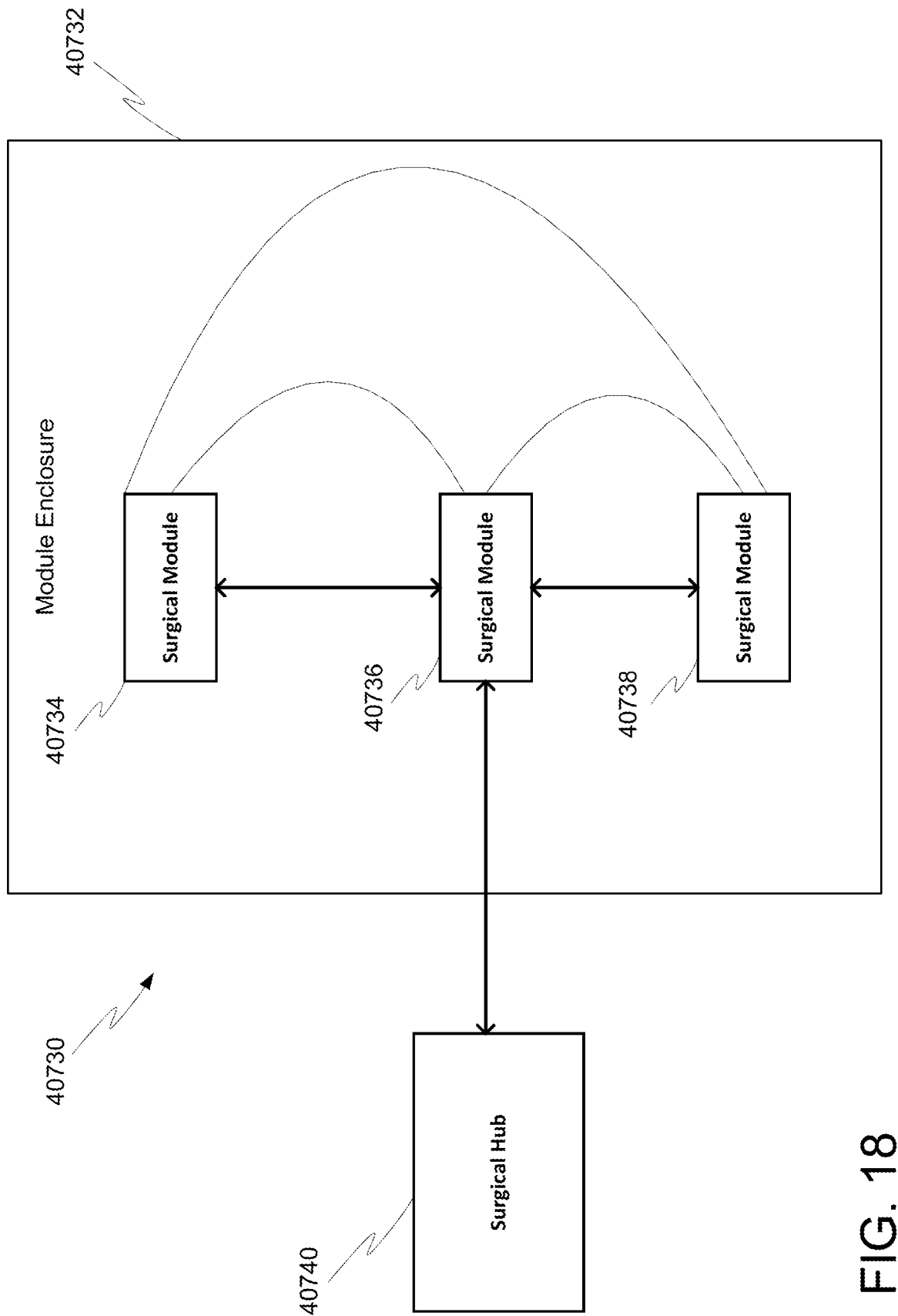
FIG. 18 shows an example of a surgical system with a module enclosure.

FIG. 18 shows an example of a surgical system 40730 with a module enclosure. The surgical system 40730 may include a modular enclosure 40732 that physically couples the surgical modules 40734, 40736, 40738. The modular enclosure 40732 may include a stacking and electrical connection. Each module enclosure 40732 may include both a physical connection mechanism and an electrical connection mechanism which may be stacked. In examples, the electrical connection may establish power and communication to each of the surgical modules 40734, 40736, 40738 within the module enclosure 40732. In examples, the electrical connection may establish communication without establishing power to each of the surgical modules 40734, 40736, 40738 within the module enclosure 40732. Each surgical module 40734, 40736, 40738 may have separate individual power plugs and a connection bus to create bus architecture for communication (not shown). The modular enclosure 40732 may include a communication or header module which includes the processing power to manage communication between the surgical modules 40734, 40736, 40738 in a surgical network or bus format. Information may be communicated to an outside edge server and/or cloud. In examples, one of the surgical modules 40734, 40736, 40738 may be a header module. The header module may include a processor which may perform additional processing and algorithm work. The header module may include a memory and/or other storage modules. The stacking of the module enclosure 40732 may be vertical or horizontal connection. The module enclosure 40732 may have a predefined enclosure with a set number of connection points for surgical modules 40734, 40736, 40738. Different module enclosures may connect with each other either wired or wirelessly to make virtual larger surgical hubs within different operating rooms. The module enclosure 40732 may include locking features that alert viable additions to the set of surgical modules 40734, 40736, 40738.

The surgical system 40730 may provide heat management based on the surgical module 40734, 40736, 40738 or surgical hub 40740 utilization. The heat buildup of the module enclosure 40732 may be used as a monitored aspect that is in turn used to change the heat generation or heat exhaust of the surgical system 40730. The surgical system 40730 may include a supplemental heat exchange or fan systems that may cool the surgical hub 40740 and the surgical modules 40734, 40736, 40738. The fans may be controlled based on the monitored heat generation of the combined surgical modules 40734, 40736, 40738 and/or surgical hub 40740. The surgical hub 40740 may instruct the individual surgical module heat exhaust systems to increase or decrease utilization as the surgical system 40730 monitors heat within a main enclosure of the module enclosure 40732. A controller may direct control of heat generation aspects of the surgical modules 40734, 40736, 40738. The controller may throttle or control aspects that are generating heat. The surgical system 40730 may switch power loads to surgical modules 40734, 40736, 40738 to control heating aspects.

Monitoring parameters from at least one of the surgical modules 40734, 40736, 40738 may be used to control or adjust at least one of the other surgical modules 40734, 40736, 40738. In examples, one of the surgical modules 40734, 40736, 40738 may be a video of a monitoring or imaging system and one of the surgical modules 40734, 40736, 40738 may be a smoke evacuator. The video of a monitoring or imaging system may be used to determine visibility issues between one time and the next, which may be used to control the increase or decrease of the smoke evacuator motor speed. Electrosurgery may create a by-product known as surgical smoke (e.g., also referred to as cautery smoke, surgical plume, diathermy plume, smoke plume, or plume). The smoke may emanate from the surgical cut site creating a potent odor, as well as reducing visibility for the surgeon. Removing surgical smoke from the air has become important (e.g., increasingly important) as electro-surgical procedures have become more common. Smoke evacuators may have fluid and solid filtering means to include particles and motors that may be operated to provide just enough evacuation to remove the smoke plume without causing other issues. Smoke evacuators may be activated via a link to the energizing of the energy device, which may cause a lag in response not proportionate to the size of the smoke plume. Influencers may contribute both an amount of smoke and type of smoke created to include tissue type, patient bio-markers, and type of device (e.g., monopolar electrosurgery, RF electrosurgery, ultrasonic cutting, a sagittal saw) selected to complete the intended task.

In examples, the surgical hub 40740 may utilize the video monitoring and/or image system to detect the type of tissue and the patient biomarkers to control the speed of the smoke evacuation and duration at which the smoke evacuation is on or off, which may minimize the smoke buildup. The operating room video system (not shown) and/or surgical hub 40740 may identify which energy device is attached or which energy device the surgeon was intending to use to control the smoke evacuation and the duration at which the smoke evacuation is on or off. The surgical hub 40740 may monitor or learn the visibility that is being displayed to the surgeon throughout the surgery and adjust the parameters on the smoke evacuation system to minimize obstruction to the surgeon based on each use of a particular instrument, tissue type, and/or knowing the next performed action of that procedure type. In examples, one of the surgical modules 40734, 40736, 40738 may be a visualization system. The visualization system may be used as a trigger and/or proportionate control of the smoke evacuator response. The denseness the smoke plume, the size of the smoke plume, and duration of the smoke plume may all relate to the amount of power needed for the smoke evacuator. The denseness the smoke plum, the size of the smoke plume, and duration of the smoke plume may be detected by the visualization system, which may communicate the information to the smoke evacuator. The smoke evacuator may use the appropriate amount of power to clear and control the smoke plume based on the information provided by the visualization system. The visualization system may (e.g., may also) detect the direction of the motion of the smoke plume as a means to adjust the control of the smoke evacuator.

In examples, the surgical hub 40740 may utilize the camera to detect micro smoke plumes and arcing of electrosurgical devices to verify an energy activation location. In examples, if using a monopolar device, using the lowest possible generator setting to achieve the desired tissue therapeutic treatment may be desired. Higher than necessary voltages may be sign that arcing is occurring. If the surgeon continues to ask for a higher voltage, this may be a signal that the integrity of the skin/dispersive pad interface is compromised. Using the visualization system to monitor aching may be used to control and/or adjust the amount of energy that is delivered. Monitoring the arching over time may be used to identify if continued energy increases are needed over a period of time. Monitoring the arching over time may be used to determine if the pad/return path is compromised. If the pad/return path is compromised, the user may be instructed to check the pad before additional power is applied. In examples, the visualization system may monitor the tip of the monopolar device (e.g., as an additional check) prior to the surgical hub 40740 adjusting the energy level of the surgical device. For example, during surgery, eschar (e.g., dead tissue from burning) may build up on the tip, in which electrical impedance increases may cause arcing, sparking, or ignition and flaming of the eschar. The visualization system may monitor the tip of the monopolar device to detect whether it has eschar buildup on the tip. If it does not have build up on the tip, the visualization system may increase the energy level. If it does have build up on the tip, the visualization system may require the user clean the monopolar device prior to allowing energy activation. In examples, the visualization system may detect the arc color. The arc color may determine the amount of power to apply to the smoke evacuator. In examples, a visual camera of the visualization system may monitor the cauterization site for released plume of steam, smoke, or aerosol.

In examples, the smoke evacuator motor may be activated based on energy handpiece activation. The tissue source and cutting method along with the type of energy device selected (e.g., ultrasonic, RF, and monopolar) may influence the smoke generated during use. The energy devices that may be used during surgery include monopolar electrosurgery, RF electrosurgery, and ultrasonic, each having different power outlets and maximum temperature limits. A higher level the power may cause a higher level of thermal spread and charring, which may generate different levels of smoke plume. Based on this information, the surgical hub 40740 may know which energy device was being used and adjust the power level of the smoke evacuator accordingly. The smoke evacuator motor speed may be adjusted based on the determined power level.

Figure 19A:
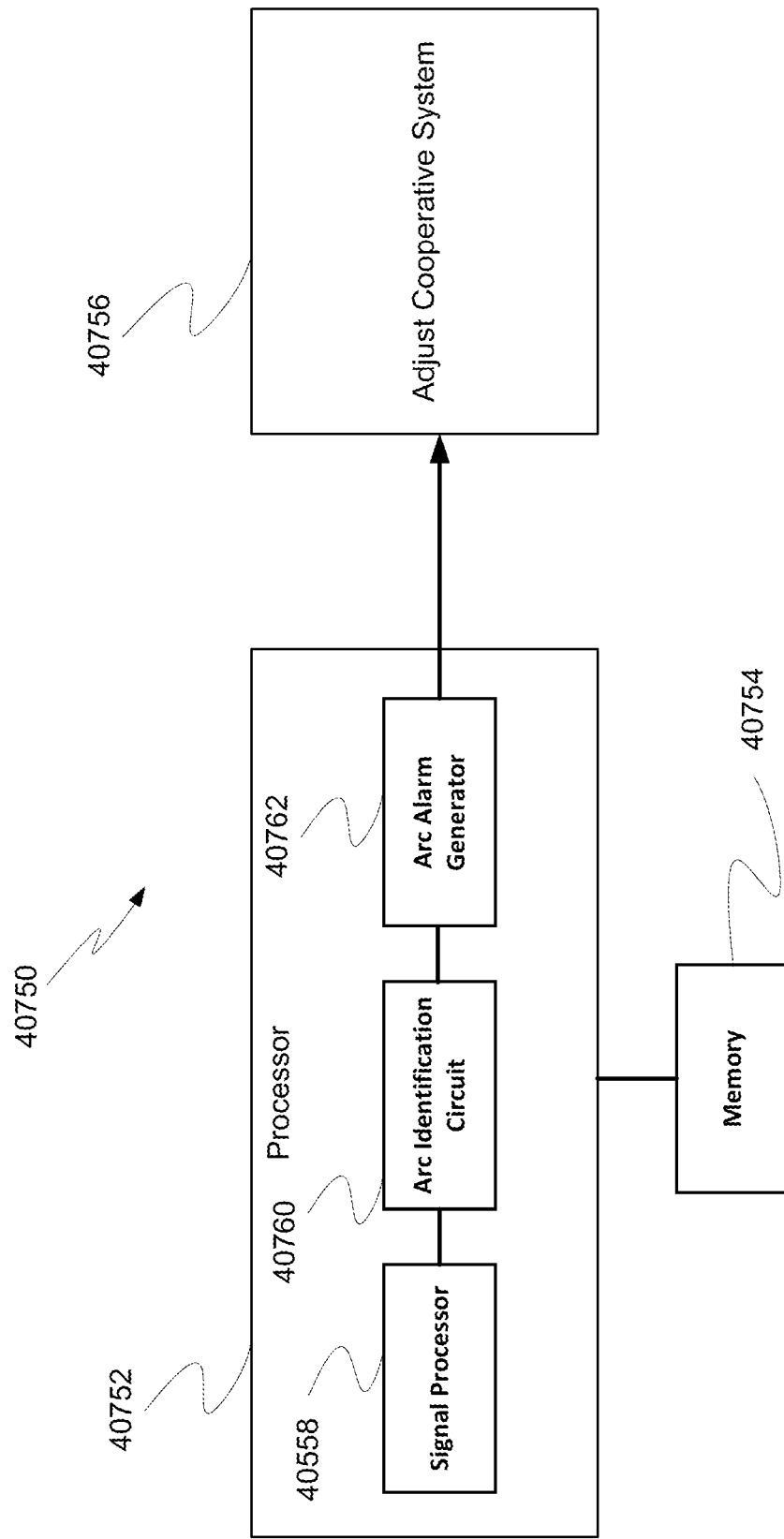
FIGS. 19A-19B show an example and a flow chart of a surgical system that detects arcing.
Figure 19B:
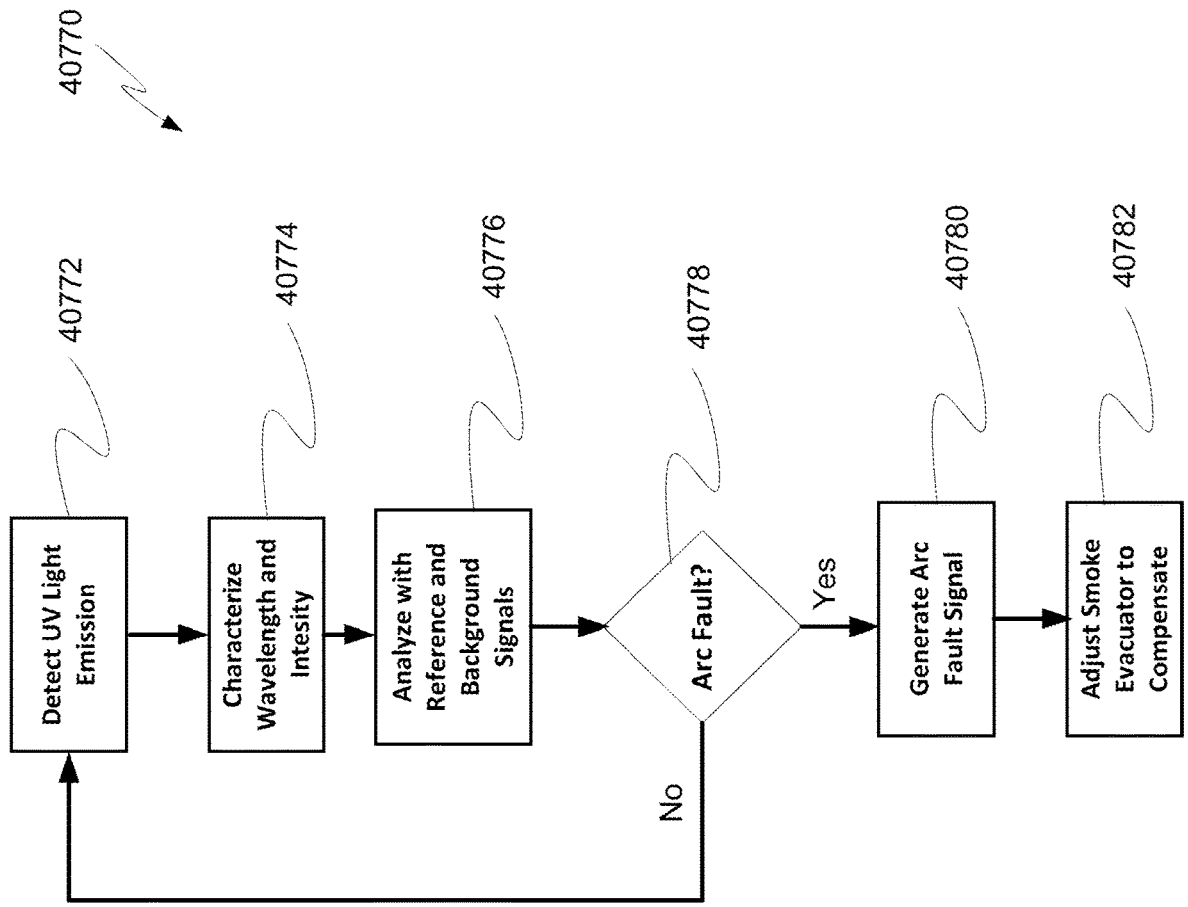

FIGS. 19A-19B show an example and flow chart of a surgical system 40750 that detects arcing. The surgical system 40750 may include a processor 40752 and a memory 40754. In examples, the processor 40752 may be a surgical hub processor. The processor 40752 may include a signal processor 40558, an arc identification circuit 40760, and an arc alarm generator 40762. If the processor 40752 detects an arcing event, it may adjust a cooperative system 40756. A flow chart 40770 may show how the processor 40752 of the surgical system 40750 detects an arcing event and adjusts the cooperative system 40756. In examples, the cooperative system 40756 may be a smoke evacuator. At 40772, the processor 40752 may detect the UV light emission. At 40774, the processor 40752 may adjust the characterize the wavelength and intensity. At 40776, the processor 40752 may analyze the arcing with reference and background signals. At 40778, the processor 40752 may determine whether or not there is an arc fault. If no at 40778, then the processor 40752 may return to detecting the UV light emission at 40772. If yes at 40778, then at 40780, the processor 40752 may generate an arc fault signal. At 40782, the processor 40752 may adjust a smoke evacuator to compensate for the arcing.

Examples described herein include a surgical hub that may detect its location within current past surgical networks. The surgical hub may reestablish necessary connections and bandwidths to support the expected protocol needs of the surgical hub. The surgical hub may detect its physical location, the network topology, and connectivity. The surgical hub may compare changes from previous uses with certain procedures and surgeons and then use it to adjust its connectivity to surgical networks to maximize its access and connection to the data stored and the surgical component it needs to support the procedure being used. The connectivity adjustments may involve connection to additional networks and parsing the data transfer needs between them to establish the overall throughput it needs to provide the data to the user from the remote locations. The connectivity adjustments may involve establishing virtual private connections to ensure the data exchanged between the remote location and the surgical hub remains at the security level necessary for the data being transferred. The connectivity adjustments may involve connection to surgical networks that may take the data of the facility and then back to the facility.

Figure 20:
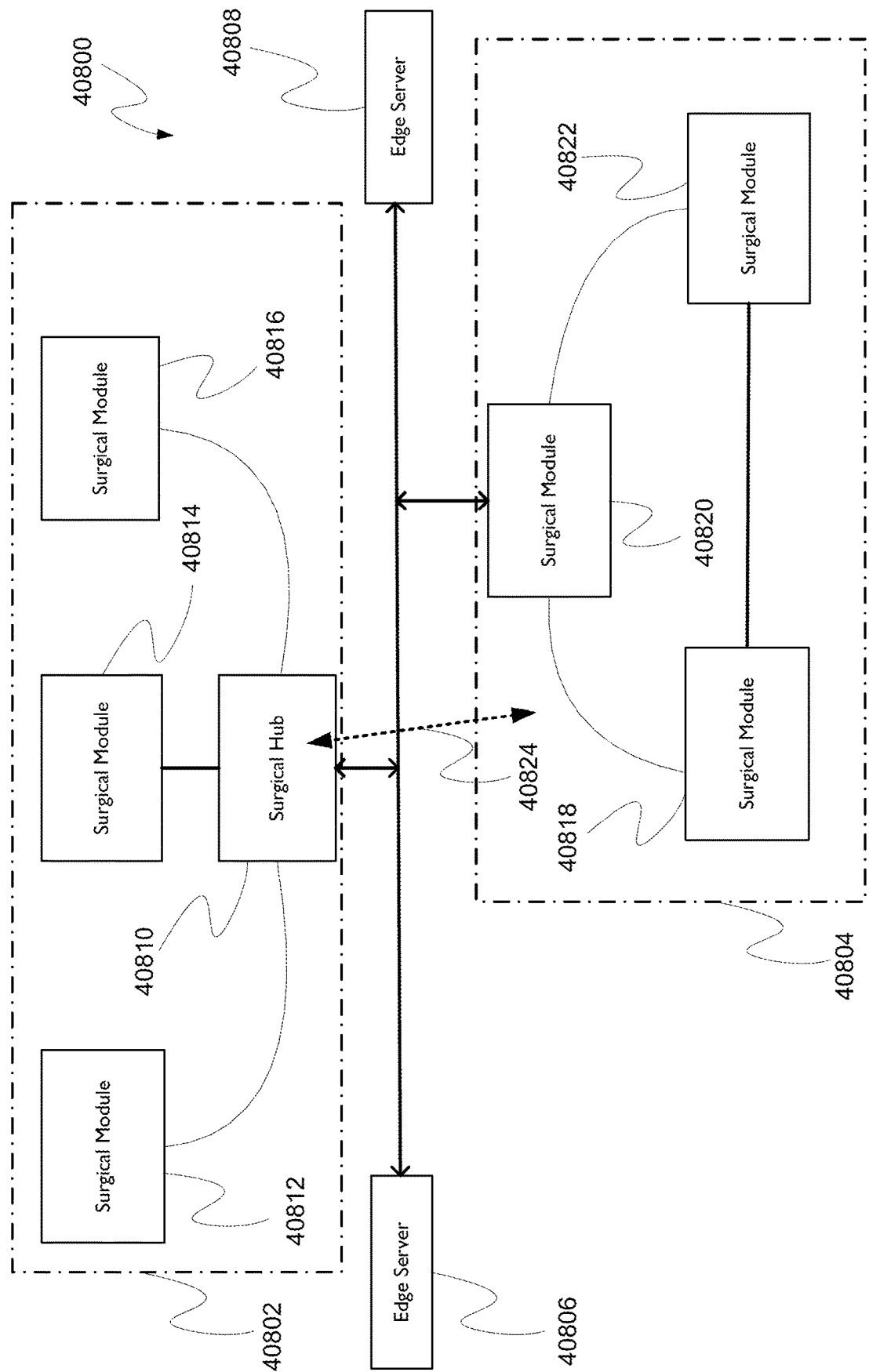
FIG. 20 shows an example of a surgical system with multiple surgical networks.

FIG. 20 shows an example of a surgical system 40800 with multiple surgical networks. The surgical system 40800 may include a first surgical network 40802 and a second surgical network 40804.

Although two surgical networks are shown in FIG. 20, the surgical system 40800 may include any number of surgical networks. In examples, the first surgical network 40802 may be the primary surgical network and the second surgical network 40804 may the secondary surgical network. The first surgical network 40802 and second surgical network 40804 may each be connected to edges servers 40806, 40808. The first surgical network 40802 may include a surgical hub 40810 and surgical modules 40812, 40814,

40816. The second surgical network 40804 may include surgical modules 40818, 40820, 40822.

The connectivity adjustments within the surgical system 40800 may be based on may be latency, data transfer parameters, bandwidth, message handling, service available, and service reliability. Latency parameters may include propagation delay, packet length and data rate, header processing size and integrity, queuing delay, and the number of interconnected systems that respond when asked for polling of addresses. The propagation delay may relate to the distance and the physical connection of the interconnected systems. The queuing delay may relate to the time a packet is waiting in the queue to be processed. The data transfer parameters may include prioritization, filtering, encryption, routing/load balancing, and data compression. The filtering may be achieved by virus scanning, intrusion detection, and/or firewalls.

The data for one surgical specialty may be different than that of other specialties. For example, the digital assets of the thoracic surgery department may include lung tumors, thoracic anatomy models, chest cavity imaging, and algorithms for interpreting, identifying, and locating thoracic tumors, transbronchial imaging systems, procedure data related to their procedures, etc. Access to this data may be needed by all the thoracic operating rooms but not any of the other operating rooms or department in the facility. However, much of this data is large and having instant access to the primary network may require significant network resources. As such, specialties and departments may have secondary networks that interconnect through the primary network rarely. Moving the secondary network assets from one network location to another network may have impacts on both the network they are moving to and the network they are moving from.

The bandwidth may relate to the maximum message payload size that can be handled by the message broker may be considered. The larger payloads may be split into multiple smaller payloads, which may create more latency and computing overhead. The service availability may relate to geographical proximity, time of day, and usage patterns. The service reliability may relate to synchronization in case of failure, swapping in case of failure, and ensuring message idempotency.

The surgical system 40800 may monitor and provide oversight to the first surgical network 40802 and the second surgical network 40804 and the edge behavior and identification of the adjustments needed. The surgical system 40800 monitoring may include monitoring the first surgical network 40802 and second surgical network 40804 for faults and issues, network congestion, direct name servers monitoring, traceroute monitoring, border gate protocol monitoring, and endpoint monitoring. The monitoring of the first surgical network 40802 and the second surgical network 40804 may include timing of restarts or reboots to establish clean protocols and the detection and elimination of faulty connections or hardware. The network congestion may include scheduling of interconnections for lower priority timing and traffic shaping control. The traffic shaping control may include smart linked systems and non-interactive traffic generators. The smart linked systems may include the sharing of traffic patterns and how much the smart system can interconnect with the surgical hub, other devices, and the cloud. The non-interactive traffic generators may include throttling or adjusting the bandwidth of devices.

The surgical system 40800 may utilize the edge servers 40806, 40808 to interact with the surgical hub 40810 and to adjust the first surgical network 40802 and the second surgical network 40804 based on the utilization and needs of the operating rooms. The utilization of the edge servers 40806, 40808 may include load sharing and smart network application. The load sharing may include a number of servers and their utilization. The load sharing may balance the traffic on a wireless or wired connection. The load sharing may introduce low throughput systems that may slow the system waiting on data to move through the lower speed of the port system. The load sharing may include a facility that may have three or more layers of distributed cooperative computing. The first surgical network 40802 may be made up the surgical hub 40810 within an operating room (not shown) which may allow the surgical hub 40810 to supervise or oversee a user's interaction with connected systems. Depending on how the other surgical networks are laid out, surgical hubs in adjacent operating rooms may share processing, stored data, or a plan. In examples the surgical system 40810 is a star network layout, the department, operating room ward, or floor may have a local central server or system that oversees the interaction of communications between the different surgical networks. In examples, the local area network (LAN) may be hooked into the main facility network which may (e.g., may also) have a primary server or edge computing server. Each level of this hierarchy may help distribute processing, share communication bandwidth, or do processing for the other levels to help prevent processing from having to be done by only the limited systems. As shown in FIG. 20, the smart network application may include an overview of the network topologies of the surgical hub 40810 to the edge servers 40806, 40808 and each topology to each of the first surgical network 40802 and the second surgical network 40804. The smart energy over internet gateway configuration may enable interconnected devices to be powered from the gateway itself.

The surgical system 40800 may detect network topology and integrate or automatically adjust the topology based on the surgical procedure, department, or staff affiliations. The network topologies may include a bus topology, a ring or dual ring topology, a mesh topology, a star topology, and a hybrid tree topology. The bus topology may include a primary backbone to the network with the surgical hub nodes (e.g., all the surgical hub nodes connected off the backbone). The ring or dual ring topology may include surgical hubs interconnected in a pass through configuration where each system may be connected in an adjacent system. The mesh topology may have nodes (e.g., every node) in the mesh connected to all of the nodes in the mesh. The star topology may have nodes (e.g., every node) connected off of a central server or node. Hybrid tree topology may have any number of networks that are interconnected via a primary topology. In examples, the hybrid tree topology may be a bus topology with other ring, bush, and mesh topologies off of the primary bus.

The interconnection of network and flow may be monitored. The location and proximity of the networks within the operating room may be physically detected. In examples, the communication parameters may be adjusted based on the connection type, distance from the surgical hub, obstacles, etc. WiFi may have frequencies between 2.5 GHz and 5 GHz. Vertical and horizontal polarized antenna array choices may provide directionality of the antennas to the communication units. The registration and location indication of a surgical network's detection or probe location be monitored in relation to other surgical networks. The surgical system 40800 may automatically detect and monitor an overall view of the network topology. In examples, the surgical system 40800 may create a view of data moving through the operating room and in between the first surgical network 40802 and the second surgical network 40804 in order to automatically adjust connected network configurations to balance the need for interconnection with the speed of communications. The surgical system 40800 may monitor and track the network flow over the procedure and between procedure.

In examples, surgical hub 40810 may be connected by surgical discipline, which may enable the surgical hub 40810 to stay within its own network to retrieve and store procedural video and interactions with staff. The surgical hub 40810 may be detected outside of the first surgical network 40802 and the establishment of a virtual private network (VPN) may connect the surgical hub 40802 back to the first surgical network 40802, even if the physical network is not directly connected to the preferred network. If the operating room area is broken into departments and each uses a mesh network, then the surgical hub 40810 may convert the department into a ring or star network configuration and behave autonomous to the first surgical network 40802 with the surgical hub 40810 being the interface. In examples, the physical wiring may be supplemented by wireless connection between the surgical hub 40810 and the surgical modules 40812, 40814, 40816, 40818, 40820, 40822 to form the hybrid network interconnection. The adjustment of the local network to a department concentric system may help minimize confusion and improve access to relevant people and files. The network utilization may be defined by the security, throughput, and type of data. Critical data or private data may be secured (e.g., encrypted) and/or sent along a more secured network.

In examples, the thoracic surgeon may normally conduct surgery in a first operating room which is in a star network off the facility's bus network, which is indicated as the first surgical network 40802 in FIG. 20. The edge servers 40806, 40806 may be interconnected to several hospitals' primary surgical networks (e.g., via a cloud). The surgeon may have a patient that requires surgery but needs CT scanning intra-surgery, so the surgery may be scheduled in a second operating room where a CT scanner is permanently installed. The second operating room may be on a different floor from the thoracic network and the imaging operating rooms may be a part of the second surgical network 40804 that may (e.g., may also) be connected to the first surgical network 40802. The surgeon may need not only the advanced energy devices commonly need, but the generator may be one of the surgical modules 40812, 40814, 40816 within the first surgical network 40802 of the first operating room. In examples, the surgeon may need a mobile robot for imaging and treatment. The mobile robot may act as a secondary hub in the thoracic operating room.

The surgical hub 40810 may be moved from the first surgical network 40802 to the second surgical network 40804, as shown by 40824. In examples, the surgical hub 40810 may be moved from the first surgical network 40802 within a thoracic surgery floor in a first operating room to the second surgical network 40804 of advanced imaging operating rooms on a different physical floor (not shown). When turned on, the surgical hub 40810 may seek to determine where it is located and to what network it is attached. If the surgical hub 40810 determines it is part of a connected but separate network from where it normally is, it may seek to establish a connection back to the first surgical network 40802. The surgical hub 40810 may do this because procedure plans, simulations, videos, and other digital aids may be stored in the first surgical network 40802 distributed between the other surgical hubs (not shown) and the thoracic surgery start server that links them all. The surgical hub 40810 may determine that the network traffic through the facility bus network is too congested for real time streaming and is (e.g., only) useful for limits bandwidth communications. To compensate for this, the surgical hub 40810 may both connect to one or more wireless LANs and connect to the first surgical network 40802 via VPNs. The VPN data may be divided between the first surgical network 40802 and the second surgical network 40804 and the surgical hub 40810 may be connected to and may send and receive data through both network connections simultaneously. The data may be encrypted and kept separated from the rest of the network traffic to ensure a stable connected and that the data is not leaked to other systems. In examples, if the certain surgical modules are detected, the network traffic may be rerouted to improve throughput, latency, and minimize packet loss and errors. This adjusted hybrid design may allow surgical hubs to share data faster and allow the machine learning to have a predefined arena to operate when reducing data.

In examples, a surgical computing device may each have a processor (not shown) configured to determine a present network locus, wherein the primary network locus is the first surgical network 40802 or a second surgical network 40804. The surgical computing device may be any of the surgical modules 40812, 40814, 40816, 40818, 40820, 40822 or the surgical hub 40810. Each of the processors may identify a data communications session and determine the surgical data type of the data communication session. The surgical data may be any of a first type of surgical data or a second type of surgical data. Based on the determination, each of processors may direct the data communications session to the first surgical network 40802 if the surgical data is the first type of surgical data or to the second surgical network 40804 if the surgical data is the second type of surgical data.

Determining whether the surgical is the first type of surgical data or the second type of surgical data may be based on the connectivity adjustments of the first surgical network 40802 and the second surgical network 40804. In examples, the connectivity adjustments may be based on latency, data transfer parameters, bandwidth, message handling, service available, or service reliability. In examples, the first surgical network 40802 may be the primary surgical network and the second surgical network 40804 may be the secondary surgical network. Each of the first surgical network 40802 and the second surgical network 40804 may be connected to the edge servers 40806, 40808. The edge servers 40806, 40808 may be connected to a surgical cloud (not shown). In examples, the first surgical network 40802 and the second network 40804 may be configured in a bus topology, a ring or dual ring topology, a mesh topology, a star topology, or a hybrid tree topology.

In examples, each of the processors of the surgical computing device may be moved from a first operating room to a second operating room. Each of the processors may be configured to determine the present network locus is different than a previous network locus. The first surgical network 40802 may be present at the first operating room and the second surgical network 40804 may be present at the second operating room.

In examples, the surgical hub 40810 may have a processor (not shown) configured to combine at least one of a first plurality of functions with at least one of a second plurality of functions to create a third surgical network (not shown). The third surgical network may be connected to the surgical hub 40810. Each of the processors of the surgical computing device may determine a present network locus of the processor. The present network locus may be any of the first surgical network 40802, the second surgical network 40804, or the third surgical network (not shown). The surgical computing device may be any of the surgical modules 40812, 40814, 40816, 40818, 40820, 40822 or the surgical hub 40810. Each of the processors may identify a data communications session and determine the surgical data type of the data communication session. The surgical data may be any of a first type of surgical data, a second type of surgical data, or a third type of surgical data. Based on the determination, each of processors may direct the data communications session to the third surgical network if the surgical data is the third type of surgical data. The determination of whether the surgical data is the third type of surgical data may be based on the connectivity adjustments of the third surgical network. The connectivity adjustments may be based on latency, data transfer parameters, bandwidth, message handling, service available, or service reliability. The first plurality and second plurality of functions may (e.g., may also) be based on latency, data transfer parameters, bandwidth, message handling, service available, or service reliability to create the third surgical network.

Figure 21:
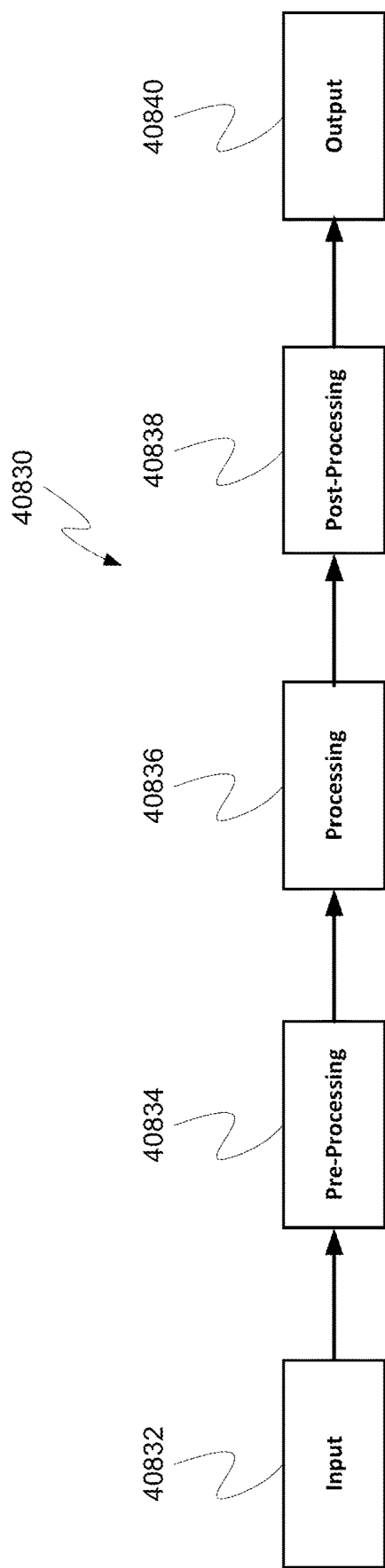
FIG. 21 shows an example surgical system that requests communication access based on subscriptions.

FIG. 21 shows an example surgical system 40830 that requests communication access based on subscriptions. Subscription based requesting access of communication access may include the prioritization of access, the scalable access to individual systems or actuators, the scalable access to individual systems or actuators, an asynchronous method, or a process control description. The input module 40832 may publish the messages on a pre-processing topic 40834. The processing module 40836 may not subscribe to the pre-processing topic 40834 to receive all messages published by the input module 40832. The processing module 40836 may act as the publisher of processing messages on the post-processing topic 40838. The output module 40840 may subscribe to this topic. The input module 40832 may publish messages on a private chat or a public chat. The private chat may be an open temporary topic. The public chat may be standard subscriber or a publisher framework.

Scalable access of individual systems or actuators may include static scaling and dynamic scaling. Static scaling may have an input line for each subscriber. Dynamic scaling may allocate lines based on current subscriber traffic. The asynchronous method may provide an advantage of the subscription based approach in that events may not have to happen at specific times and/or things are not running off the same clock or time frame. The publisher may publish at its discretion to the broker. The subscriber may then permit to view or see subject matter at a time most appropriate to the subscriber. This could be at a computational low period or during idle cycles, which may allow for greater flexibility when the system does not have to follow the same clocking sequence. The process control description may include a publisher, subscriber, and broker. The publisher may be the supplier of information or messages. The subscriber may be the consumer of information. The broker may decouple communication between devices that publish information and other devices that subscribe to the information.

Figure 22:
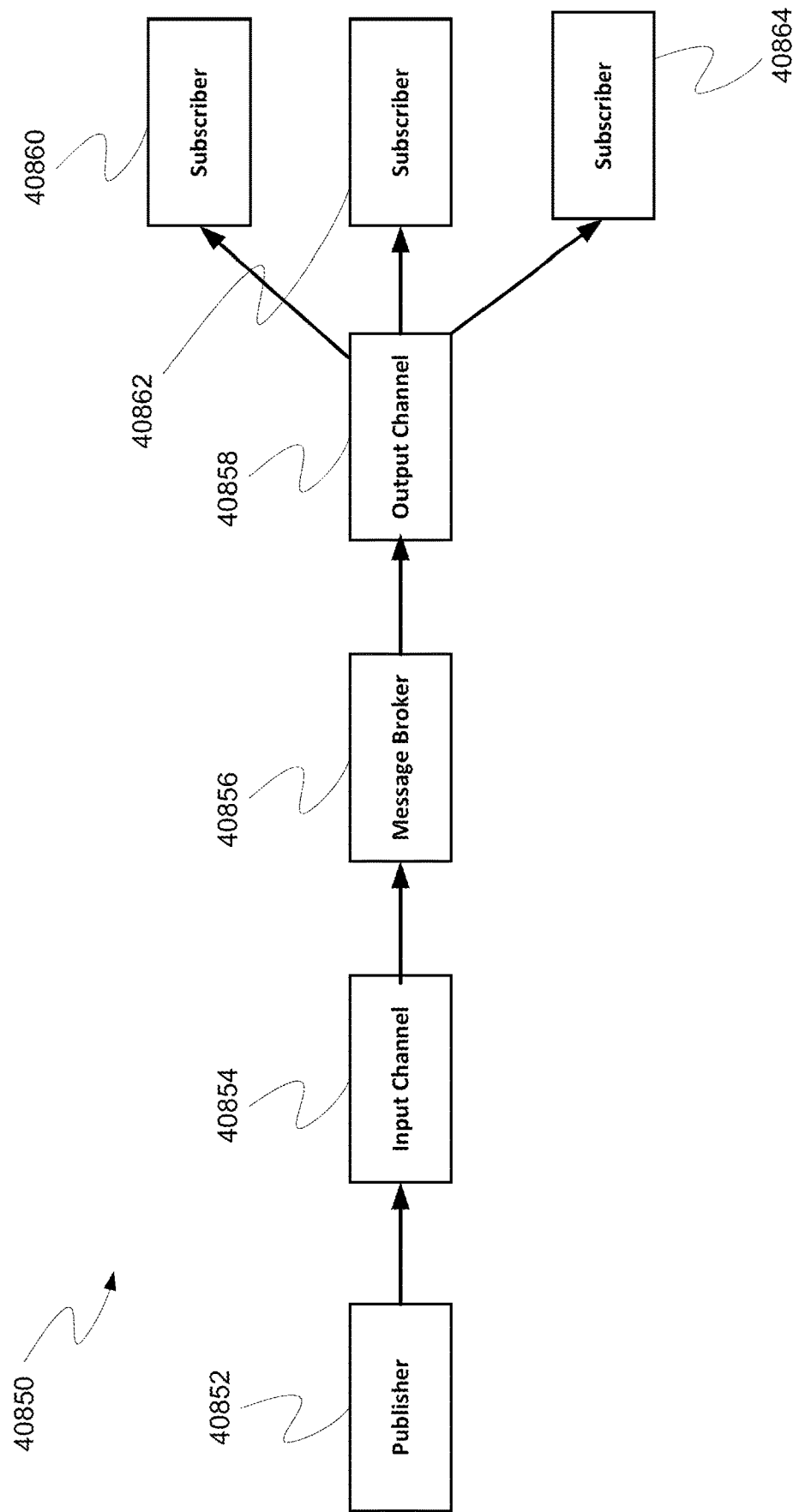
FIG. 22 shows an example of a surgical system 40850 that publishes information to a broker.

FIG. 22 shows an example of a surgical system 40850 that publishes information to a broker. The surgical system 40850 may include a publisher 40852. The publisher 40852 may input information via an input channel 40854 to a broker 40856. The broker 40856 may output the information via an output channel 40856 to subscribers 40860, 40862, 40864. In examples, in podcasts, the publisher 40852 (e.g., the content creator) may upload (e.g., publish) the latest version of a podcast to "google podcasts" (e.g., broker 40856). Users that follow or subscribe (e.g., the subscribers 40860, 40862, 40864) to the podcast to the podcast may be alerted that new content is available. The subscribers 40860, 40862, 40864 may then go to "google podcasts" and watch or listen to the content. In examples, surgical hubs may publish the updated list or devices within the operating room boundaries to the broker area. The broker 40856 may ping the connected devices in the operating rooms (e.g., all the operating rooms) that have subscribed to a subject or channel. The devices may pull the information during an idle period and each device may know the others in the operating room.

The invention claimed is:

1. A first surgical module for use within a surgical system, comprising:
a first port connected to a surgical hub, wherein the first port comprises a control plane, a data plane, and a backplane that facilitates data communication between the first surgical module and the surgical hub;
a second port connected to a second surgical module, wherein the second port comprises an external wire that facilitates data communication between the first surgical module and the second surgical module; and
a controller configured to:
receive, via the first port, a first indication from the surgical hub that the second surgical module is energized to perform a first surgical task;
based on receiving the first indication, prevent the first surgical module from performing a second surgical task;
based on receiving the first indication, instruct the first surgical module to perform a third surgical task;
send, via a second port, a second indication to the second surgical module that the first surgical module is prevented from performing the second surgical task and is instructed to perform the third surgical task; and
send, via the first port, a third indication to the surgical hub that the first surgical module is prevented from performing the second surgical task and is performing the third surgical task.

2. The first surgical module of claim 1, wherein the second port is isolated from the surgical hub.

3. The first surgical module of claim 1, wherein the first surgical module is set up in bipolar configuration and the second surgical module is set up in a monopolar configuration.

4. The first surgical module of claim 3, wherein the surgical hub increases input voltage to the first surgical module based on the second surgical module being set up in a monopolar configuration and the first surgical module being prevented from performing the second surgical task.

5. The first surgical module of claim 3, wherein the second surgical module is a smoke evacuator module, and the first surgical module is an advanced visualization module.

6. The first surgical module of claim 5, wherein:
the first surgical task is to pull smoke from a surgical site,
the second surgical task is to increase resolution,
the third surgical task is to increase an intensity of light,
the smoke evacuator module is energized to pull the smoke from the surgical site,
the advanced visualization module is prevented from increasing the resolution, and
the advanced visualization module is instructed to increase the intensity of light.

7. The first surgical module of claim 1, wherein the second surgical module is a smoke evacuator and the first surgical module is at least one of a visualization system, a generator, a header, a monitoring or imaging system, or an insufflation system.

8. A first surgical module for use within a surgical system, comprising:
a first port connected to a surgical hub, wherein the first port comprises a control plane, a data plane, and a backplane that facilitates data communication between the first surgical module and the surgical hub;
a second port connected to a second surgical module, wherein the second port comprises an external wire that facilitates data communication between the first surgical module and the second surgical module; and
a controller configured to:
receive, via the first port, a first indication from the surgical hub that the second surgical module is energized to perform a first surgical task;
based on receiving the first indication, prevent the first surgical module from performing a second surgical task;
send, via a second port, a second indication to the second surgical module that the first surgical module is prevented from performing the second surgical task; and
send, via the first port, a third indication to the surgical hub that the first surgical module is prevented from performing the second surgical task.

9. The first surgical module of claim 8, wherein the second port is isolated from the surgical hub.

10. The first surgical module of claim 8, wherein the first surgical module is set up in bipolar configuration and the second surgical module is set up in a monopolar configuration.

11. The first surgical module of claim 10, wherein the surgical hub increases input voltage to the first surgical module based on the second surgical module being set up in a monopolar configuration and the first surgical module being prevented from performing the second surgical task.

12. The first surgical module of claim 10, wherein the second surgical module is a smoke evacuator module, and the first surgical module is an advanced visualization module.

13. The first surgical module of claim 12, wherein:
the first surgical task is to pull smoke from a surgical site,
the second surgical task is to increase resolution,
the smoke evacuator module is energized to pull the smoke from the surgical site, and
the advanced visualization module is prevented from increasing the resolution.

14. A surgical system, comprising:
a surgical hub;
a surgical power system configured to power the surgical hub;
a first surgical module, comprising:
a first port connected to the surgical hub, wherein the first port comprises a control plane, a data plane, and a backplane that facilitates data communication between the first surgical module and the surgical hub;
a second port connected to a second surgical module, wherein the second port comprises an external wire that facilitates data communication between the first surgical module and the second surgical module; and
a controller configured to:
receive, via the first port, a first indication from the surgical hub that the second surgical module is energized to perform a first surgical task;
based on receiving the first indication, prevent the first surgical module from performing a second surgical task;
based on receiving the first indication, instruct the first surgical module to perform a third surgical task;
send, via a second port, a second indication to the second surgical module that the first surgical module is prevented from performing the second surgical task and is instructed to perform the third surgical task; and
send, via the first port, a third indication to the surgical hub that the first surgical module is prevented from performing the second surgical task and is performing the third surgical task.

15. The surgical system of claim 14, wherein the second port is isolated from the surgical hub.

16. The surgical system of claim 14, wherein the first surgical module is set up in a bipolar configuration and the second surgical module is set up in a monopolar configuration.

17. The surgical system of claim 16, wherein the surgical hub increases input voltage to the first surgical module based on the second surgical module being set up in a monopolar configuration and the first surgical module being prevented from performing the second surgical task.

18. The surgical system of claim 16, wherein the second surgical module is a smoke evacuator module, and the first surgical module is an advanced visualization module.

19. The surgical system of claim 18, wherein:
the first surgical task is to pull smoke from a surgical site,
the second surgical task is to increase resolution,
the third surgical task is to increase an intensity of light,
the smoke evacuator module is energized to pull the smoke from the surgical site,
the advanced visualization module is prevented from increasing the resolution, and
the advanced visualization module is instructed to increase the intensity of light.

20. The surgical system of claim 14, wherein the second surgical module is a smoke evacuator and the first surgical module is at least one of a smoke evacuator, a visualization system, a generator, a header, a monitoring or imaging system, or an insufflation system.

* * * * *